(12) United States Patent
Masciotti et al.

(10) Patent No.: US 12,414,714 B2
(45) Date of Patent: Sep. 16, 2025

(54) SYSTEM AND METHOD FOR CONTINUOUS AND ON-DEMAND ANALYTE MONITORING

(71) Applicant: Senseonics, Incorporated, Germantown, MD (US)

(72) Inventors: James Masciotti, Germantown, MD (US); Abhi Chavan, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 396 days.

(21) Appl. No.: 17/872,789

(22) Filed: Jul. 25, 2022

(65) Prior Publication Data

US 2022/0361781 A1    Nov. 17, 2022

Related U.S. Application Data

(62) Division of application No. 16/709,140, filed on Dec. 10, 2019, now Pat. No. 11,452,467.

(60) Provisional application No. 62/777,583, filed on Dec. 10, 2018.

(51) Int. Cl.
| | | |
|---|---|---|
| A61B 5/145 | (2006.01) | |
| A61B 5/00 | (2006.01) | |
| H04W 4/80 | (2018.01) | |

(52) U.S. Cl.
CPC ........ *A61B 5/14532* (2013.01); *A61B 5/0022* (2013.01); *A61B 5/6824* (2013.01); *A61B 5/742* (2013.01); *H04W 4/80* (2018.02); *A61B 2562/0271* (2013.01)

(58) Field of Classification Search
None
See application file for complete search history.

(56) References Cited

U.S. PATENT DOCUMENTS

| | | |
|---|---|---|
| 7,003,341 B2 | 2/2006 | Say et al. |
| 8,073,548 B2 | 12/2011 | Colvin, Jr. et al. |
| 9,414,775 B2 | 8/2016 | Colvin, Jr. et al. |
| 9,693,714 B2 | 7/2017 | DeHennis et al. |
| 10,177,609 B2 | 1/2019 | Olson et al. |
| 2009/0112154 A1 | 4/2009 | Montgomery et al. |
| 2011/0213225 A1 | 9/2011 | Bernstein et al. |
| 2013/0117696 A1 | 5/2013 | Robertson et al. |

(Continued)

FOREIGN PATENT DOCUMENTS

| | | |
|---|---|---|
| JP | 2013-502978 A | 1/2013 |
| JP | 2017-504446 A | 2/2017 |

(Continued)

*Primary Examiner* — Jay B Shah
(74) *Attorney, Agent, or Firm* — Rothwell, Figg, Ernst & Manbeck, P.C.

(57) ABSTRACT

An analyte monitoring system includes an analyte sensor, a transceiver, and a display device. The analyte sensor may include an analyte indicator that exhibits one or more detectable properties based on an amount or concentration of an analyte in proximity to the analyte indicator. The transceiver may receive first sensor data directly from the analyte sensor and may calculate first analyte information using at least the received first sensor data. The display device may receive second sensor data directly from the analyte sensor and calculates second analyte information using at least the received second sensor data. The transceiver may convey the first analyte information, and the display device may receive the first analyte information conveyed by the transceiver and display the first and second analyte information.

34 Claims, 12 Drawing Sheets

(56) References Cited

U.S. PATENT DOCUMENTS

| | | |
|---|---|---|
| 2013/0241745 A1 | 9/2013 | Colvin, Jr. et al. |
| 2015/0123641 A1 | 5/2015 | Dalton et al. |
| 2015/0182115 A1 | 7/2015 | DeHennis |
| 2016/0015267 A1 | 1/2016 | Bernstein et al. |
| 2016/0015268 A1 | 1/2016 | Bernstein et al. |
| 2016/0015303 A1 | 1/2016 | Bernstein et al. |
| 2018/0103879 A1 | 4/2018 | Masciotti et al. |
| 2018/0110077 A1 | 4/2018 | Mandapaka et al. |
| 2018/0360355 A1 | 12/2018 | Chavan et al. |
| 2019/0125969 A1 | 5/2019 | Montgomery et al. |
| 2020/0100676 A1 | 4/2020 | Bernstein et al. |
| 2022/0359074 A1 | 11/2022 | Bernstein et al. |
| 2023/0238131 A1 | 7/2023 | Bernstein et al. |
| 2023/0268071 A1 | 8/2023 | Bernstein et al. |

FOREIGN PATENT DOCUMENTS

| | | |
|---|---|---|
| WO | 2015/084947 A1 | 6/2015 |
| WO | 2017/172781 A1 | 10/2017 |

SYSTEM AND METHOD FOR CONTINUOUS AND ON-DEMAND ANALYTE MONITORING

CROSS-REFERENCE TO RELATED APPLICATIONS

The present application is a divisional of U.S. application Ser. No. 16/709,140, filed Dec. 10, 2019, which claims the benefit of priority to U.S. Provisional Application Ser. No. 62/777,583, filed on Dec. 10, 2018, which are incorporated herein by reference in their entireties.

BACKGROUND

Field of Invention

The present disclosure relates to an analyte monitoring system and method. More specifically, aspects of the present disclosure relate to an analyte monitoring system for continuous and on-demand analyte monitoring.

Discussion of the Background

Analyte monitoring systems may be used to measure analyte levels, such as analyte concentrations. One type of analyte monitoring system is a continuous glucose monitoring (CGM) system. A CGM system measures glucose levels throughout the day and can be very useful in the management of diabetes.

Some CGM systems include an analyte sensor and a transmitter that are worn by the patient. In some examples, the analyte sensor and the transmitter are worn on either the arm or the stomach of the host, which typically require some type of tape or strap to ensure the analyte sensor and transmitter remain mounted to the skin of the patient. While using a CGM system is helpful for the patient to manage his or her glucose levels, continuously wearing an analyte sensor or a transmitter throughout the day can be cumbersome for the patient, interfering with the patient's daily activities. Accordingly, improved analyte monitoring systems and methods are needed.

SUMMARY

The present invention overcomes the disadvantages of prior systems by providing, among other advantages, more flexibility in choosing when to wear or use the analyte monitoring system while still providing the patient the ability to monitor his or her glucose levels at any time. In some embodiments, the present invention may provide an improved analyte monitoring system that operates under two or more modes, including a continuous glucose monitoring mode and a flash glucose monitoring mode (e.g., on-demand request for sensor data). A user or patient may select the analyte monitoring system to operate under either the continuous glucose monitoring mode or the flash glucose monitoring mode, as desired.

One aspect of the invention may provide an analyte monitoring system including an analyte sensor, a transceiver, and a display device. The analyte sensor may include an analyte indicator that exhibits one or more detectable properties based on an amount or concentration of an analyte in proximity to the analyte indicator. The transceiver may be configured to receive first sensor data directly from the analyte sensor, calculate first analyte information using at least the received first sensor data, and convey the first analyte information. The display device may be configured to receive second sensor data conveyed from the analyte sensor, calculate analyte information using at least the received second sensor data, receive the first analyte information conveyed by the transceiver, and display the first and second analyte information.

In some embodiments, the display device may include a first wireless communication integrated-circuit (IC) and a second wireless communication IC. In some embodiments, the first communication IC may be configured to employ a first standard to communicate wirelessly, the second communication IC may be configured to employ a second standard to communicate wirelessly, and the second standard may be different than the first standard. In some embodiments, the first standard is a Bluetooth standard, and the second standard is a near field communication (NFC) standard. In some embodiments, the display device may be configured to use the first wireless communication IC to receive the first analyte information conveyed by the transceiver, and the display device may be configured to use the second wireless communication IC to receive the second sensor data directly from the analyte sensor. In some embodiments, the display device may include a third wireless communication IC, and the display device may be configured to use the third wireless communication IC to convey the first and second analyte information over a network to a remote device.

In some embodiments, the transceiver may be worn by a host using the analyte sensor while the transceiver receives the first sensor data directly from the analyte sensor. In some embodiments, the display device may include a graphical user interface and may be configured to generate an alert or alarm on the graphical user interface of the display device. In some embodiments, the transceiver may include a graphical user interface and may be configured to generate an alert or alarm on the graphical user interface of the transceiver. In some embodiments, the display device may be configured to convey the second analyte information to the transceiver, and the transceiver may be configured to receive the second analyte information.

In some embodiments, the display device may be configured to receive one or more calibration points. In some embodiments, the display device may be configured to perform an analyte information calibration using at least the one or more calibration points. In some embodiments, the display device may be configured convey the one or more calibration points, and the transceiver may be configured to receive the one or more calibration points and perform an analyte information calibration using at least the one or more calibration points.

In some embodiments, one or more of the first and second analyte information may include one or more of: (i) an analyte concentration, (ii) a time stamp, and (iii) an analyte concentration trend information. In some embodiments, one or more of the first and second analyte information may include one or more of: (i) an alert, (ii) an alarm, and (iii) a notification.

In some embodiments, the first sensor data may include one or more of: (i) a measurement of the one or more detectable properties and (ii) a temperature measurement.

Another aspect of the present invention may provide a method for using analyte monitoring system. The method may include a step (a) of using a transceiver of an analyte monitoring system to receive first sensor data directly from an analyte sensor of the analyte monitoring system. The method may include a step (b) of using the transceiver to calculate first analyte information using at least the first sensor data. The method may include a step (c) of using the transceiver to convey the first analyte information. The method may include a step (d) of using a display device of the analyte monitoring system to receive the first analyte information conveyed by the transceiver. The method may include a step (e) of using the display device to receive second sensor data directly from the analyte sensor. The method may include a step (f) of using the display device to calculate second analyte information using at least the received second sensor data. The method may include a step (g) of using the display device of using the display device to display the first analyte information and the second analyte information.

In some embodiments, the step (a) may include positioning the transceiver such that the transceiver is operatively linked to the analyte sensor. In some embodiments, positioning the transceiver may include wearing, by a host using the analyte sensor, the transceiver externally on an armband, a wrist band, a waist band, or an adhesive patch. In some embodiments, the step (e) may include positioning the display device such that the display device is operatively linked to analyte sensor. In some embodiments, the step (e) may include removing the transceiver away from the analyte sensor such that the transceiver is not operatively linked to the analyte sensor.

In some embodiments, the display device may include a first wireless communication IC and a second wireless communication IC, and the first communication IC may be configured to employ a first standard to communicate wirelessly, the second communication IC may be configured to employ a second standard to communicate wirelessly, and the second standard may be different than the first standard. In some embodiments, the first standard may be a Bluetooth standard, and the second standard may be a near field communication (NFC) standard. In some embodiments, the step (c) may include using the first communication IC of the display device to receive the first analyte information conveyed by the transceiver. In some embodiments, the step (e) may include using the second communication IC of the display device to receive the second sensor data directly from the sensor. In some embodiments, the display device may include a third wireless communication IC, and the method may include using the third wireless communication IC to convey the first analyte information and the second analyte information over a network to a remote device.

In some embodiments, one or more of the first and second analyte information may include one or more of: (i) an analyte concentration, (ii) a time stamp, and (iii) analyte concentration trend information. In some embodiments, one or more of the first and second analyte information may include one or more of: (i) an alert, (ii) an alarm, and (iii) a notification. In some embodiments, the first sensor data may include one or more of: (i) a measurement of one or more detectable properties exhibited by an analyte indicator of the analyte sensor based on an amount or concentration of an analyte in proximity to the analyte indicator and (ii) a temperature measurement.

In some embodiments, the display device may include a graphical user interface and may be configured to generate an alert or alarm on the graphical user interface of the display device. In some embodiments, the transceiver may include a graphical user interface and may be configured to generate an alert or alarm on the graphical user interface of the transceiver. In some embodiments, the method may further include using the display device to convey the second analyte information and using the transceiver to receive the second analyte information conveyed by the display device.

In some embodiments, the method may further include using the display device to receive one or more calibration points. In some embodiments, the method may further include using the display device to perform an analyte information calibration using at least the one or more calibration points. In some embodiments, the method may further include using the display device to convey the one or more calibration points, and the method may further include using the transceiver to receive the one or more calibration points conveyed by the display device and perform an analyte information calibration using at least the one or more calibration points.

Another aspect of the present invention may provide an analyte monitoring system comprising an analyte sensor, a transceiver, and a display device. The analyte sensor may include an analyte indicator that exhibits one or more detectable properties based on an amount or concentration of an analyte in proximity to the analyte indicator. The transceiver may be configured to receive first sensor data directly from the analyte sensor and to convey the first sensor data. The display device may be configured to receive the first sensor data conveyed by the transceiver, calculate first analyte information using at least the received first sensor data, receive second sensor data directly from the analyte sensor, calculate second analyte information using at least the received second sensor data, and display the first and second analyte information.

In some embodiments, the display device may include a first wireless communication integrated-circuit (IC) and a second wireless communication IC. In some embodiments, the first communication IC may be configured to employ a first standard to communicate wirelessly, the second communication IC may be configured employ a second standard to communicate wirelessly, and the second standard may be different than the first standard. In some embodiments, the first standard is a Bluetooth standard, and the second standard is a near field communication (NFC) standard. In some embodiments, the display device may be configured to use the first wireless communication IC to receive the first sensor data conveyed by the transceiver, and the display device may be configured to use the second wireless communication IC to receive the second sensor data directly from the analyte sensor. In some embodiments, the display device may include a third wireless communication IC, and the display device may be configured to use the third wireless communication IC to convey the first and second analyte information over a network to a remote device.

Another aspect of the present invention may provide a method of using an analyte monitoring system. The method may include a step (a) of using a transceiver of an analyte monitoring system to receive first sensor data directly from an analyte sensor of the analyte monitoring system. The method may include a step (b) of using the transceiver to convey the first analyte information. The method may include a step (c) of using a display device of the analyte monitoring system to receive the first sensor data conveyed by the transceiver. The method may include a step (d) of using the display device to calculate first analyte information using at least the first sensor data. The method may include a step (e) of using the display device to receive second sensor data directly from the analyte sensor. The method may include a step (f) of using the display device to calculate second analyte information using at least the received second sensor data. The method may include a step (g) of using the display device to display the first analyte information and the second analyte information.

In some embodiments, the step (a) may include positioning the transceiver such that the transceiver is operatively linked to the analyte sensor. In some embodiments, positioning the transceiver may include wearing, by a host using the analyte sensor, the transceiver externally on an armband, a wrist band, a waist band, or an adhesive patch.

In some embodiments, the step (e) may include positioning the display device such that the display device is operatively linked to analyte sensor. In some embodiments, the step (e) may include using the second communication IC of the display device to receive the second sensor data from the analyte sensor.

In some embodiments, the display device may include a first wireless communication IC and a second wireless communication IC, the first communication IC may be configured to employ a first standard to communicate wirelessly, the second communication IC may be configured to employ a second standard to communicate wirelessly, and the second standard may be different than the first standard. In some embodiments, the first standard may be a Bluetooth standard, and the second standard may be a near field communication (NFC) standard. In some embodiments, the step (b) may include using the first communication IC of the display device to receive the first analyte sensor from the transceiver.

In some embodiments, the display device may include a third wireless communication IC, and the method may further include using the third wireless communication of the display device to convey the first analyte information and the second analyte information over a network to a remote device. In some embodiments, one or more of the first and second analyte information may include one or more of: (i) an analyte concentration, (ii) a time stamp, and (iii) analyte concentration trend information. In some embodiments, the first and second analyte information may include one or more of: (i) an alert, (ii) an alarm, and (iii) a notification. In some embodiments, the first sensor data may include one or more of: (i) a measurement of the one or more detectable properties exhibited by an analyte indicator of the analyte sensor based on an amount or concentration of an analyte in proximity to the analyte indicator and (ii) a temperature measurement.

In some embodiments, the display device may include a graphical user interface and may be configured to generate an alert or alarm on the graphical user interface of the display device. In some embodiments, the transceiver comprises a graphical user interface and is configured to generate an alert or alarm on the graphical user interface of the transceiver. In some embodiments, the method may further include using the display device to convey the second analyte information to the transceiver. In some embodiments, the method may further include using the display device to receive one or more calibration points. In some embodiments, the method may further include using the display device to perform an analyte information calibration using at least the one or more calibration points.

Another aspect of the invention may provide a display device. The display device may include a first wireless communication integrated circuit (IC) configured to employ a first standard to communicate wirelessly with a transceiver and to receive first analyte information from the transceiver. The display device may include a second wireless communication IC configured to employ a second standard to communicate wirelessly and directly with an analyte sensor and to receive sensor data directly from the analyte sensor, and the second standard may be different than the first standard. The display device may include a graphical user interface. The display device may include a computer including a non-transitory memory and a processor. The computer may be configured to calculate second analyte information using at least the received second sensor data and to display the first and second analyte information using the graphical user interface.

Another aspect of the invention may provide a display device. The display device may include a first wireless communication integrated circuit (IC) configured to employ a first standard to communicate wirelessly with a transceiver and to receive first sensor data from the transceiver. The display device may include a second wireless communication IC configured to employ a second standard to communicate wirelessly and directly with an analyte sensor and to receive second sensor data directly from the analyte sensor, and the second standard may be different than the first standard. The display device may include a graphical user interface. The display device may include a computer including a non-transitory memory and a processor. The display device may be configured to: (i) calculate first analyte information using at least the received first sensor data, (ii) calculate second analyte information using at least the received second sensor data, and (iii) display the first and second analyte information using the graphical user interface.

These and other embodiments encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
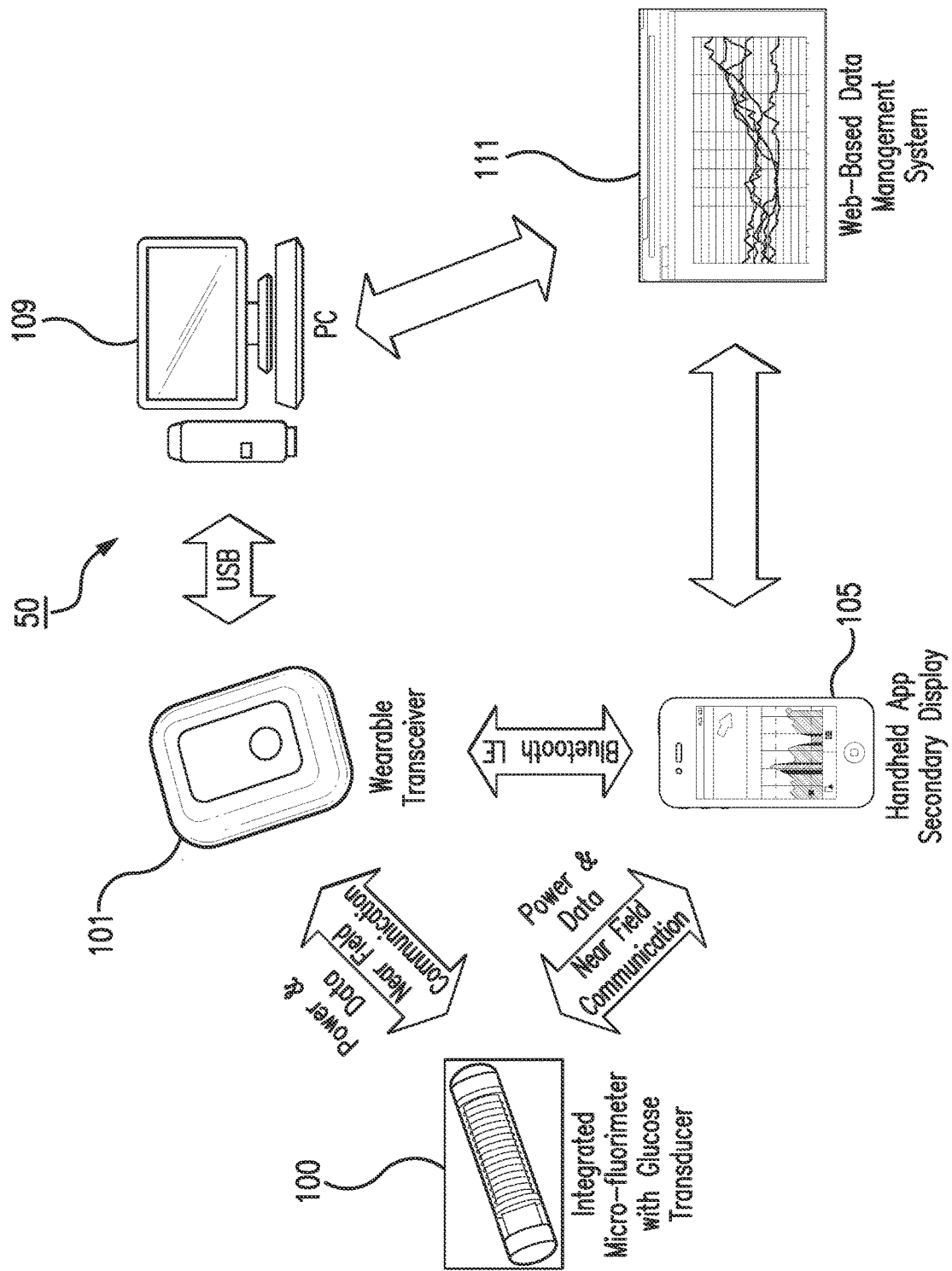
FIG. 1 illustrates a schematic view of an analyte monitoring system embodying aspects of the present invention.

FIG. 1 is a schematic view of an exemplary analyte monitoring system 50 embodying aspects of the present invention. In some embodiments, the analyte monitoring system 50 may be a continuous analyte monitoring system (e.g., a continuous glucose monitoring system). In some embodiments, the analyte monitoring system 50 may be an on-demand monitoring system. In some embodiments, the analyte monitoring system 50 may include one or more of an analyte sensor 100, a transceiver 101, a display device 105, a personal computer 109, and a data management system 111 hosted by a remote server or network attached storage hardware.

In some embodiments, the sensor 100 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone). In some embodiments, the analyte monitoring system 50 may include a web interface for plotting and sharing of uploaded data.

Figure 2:
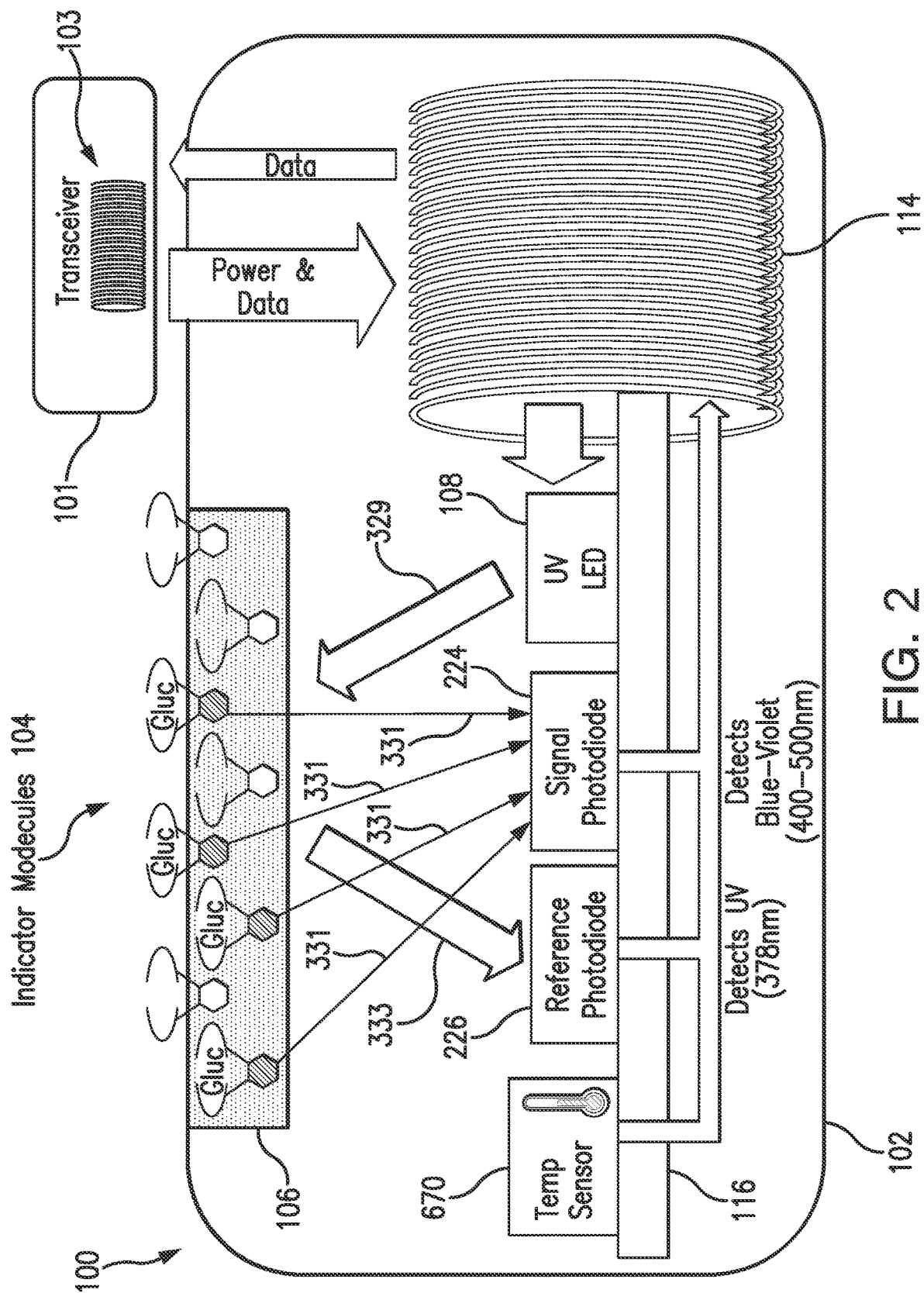
FIG. 2 illustrates a schematic view of a sensor and transceiver of an analyte monitoring system embodying aspects of the present invention.

In some embodiments, as illustrated in FIG. 2, the transceiver 101 may include an inductor 103, such as, for example, a coil. The transceiver 101 may generate an electromagnetic wave or electrodynamic field (e.g., by using a coil) to induce a current in an inductor 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive sensor data (e.g., measurement information) directly from the sensor 100. For example, in a non-limiting embodiment, the transceiver 101 may receive sensor data by detecting modulations in the electromagnetic wave generated by the sensor 100, e.g., by detecting modulations in the current flowing through the coil 103 of the transceiver 101.

The inductor 103 of the transceiver 101 and the inductor 114 of the sensor 100 may be in any configuration that permits adequate field strength to be achieved when the two inductors are brought within adequate physical proximity.

In some non-limiting embodiments, as illustrated in FIG. 2, the sensor 100 may be encased in a sensor housing 102 (i.e., body, shell, capsule, or encasement), which may be rigid and biocompatible. The sensor 100 may include an analyte indicator 106, such as, for example, a polymer graft coated, diffused, adhered, or embedded on or in at least a portion of the exterior surface of the sensor housing 102. The analyte indicator 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/ or other electronic components (e.g., a non-volatile memory), may be fabricated in the semiconductor substrate 116 with the remainder of the circuitry is secured to the semiconductor substrate 116 and/or a core (e.g., ferrite core) for the inductor 114. In some embodiments, the semiconductor substrate 116 and/or a core may provide communication paths between the various secured components.

In some embodiments, the one or more of the sensor housing 102, analyte indicator 106, indicator molecules 104, light source 108, photodetectors 224, 226, temperature transducer 670, substrate 116, and inductor 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductors 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductor 114), the transceiver interface device may include the antenna (e.g., inductor 114) of sensor 100. In some of the transcutaneous embodiments where there exists a wired connection between the sensor 100 and the transceiver 101, the transceiver interface device may include the wired connection.

Figure 3:
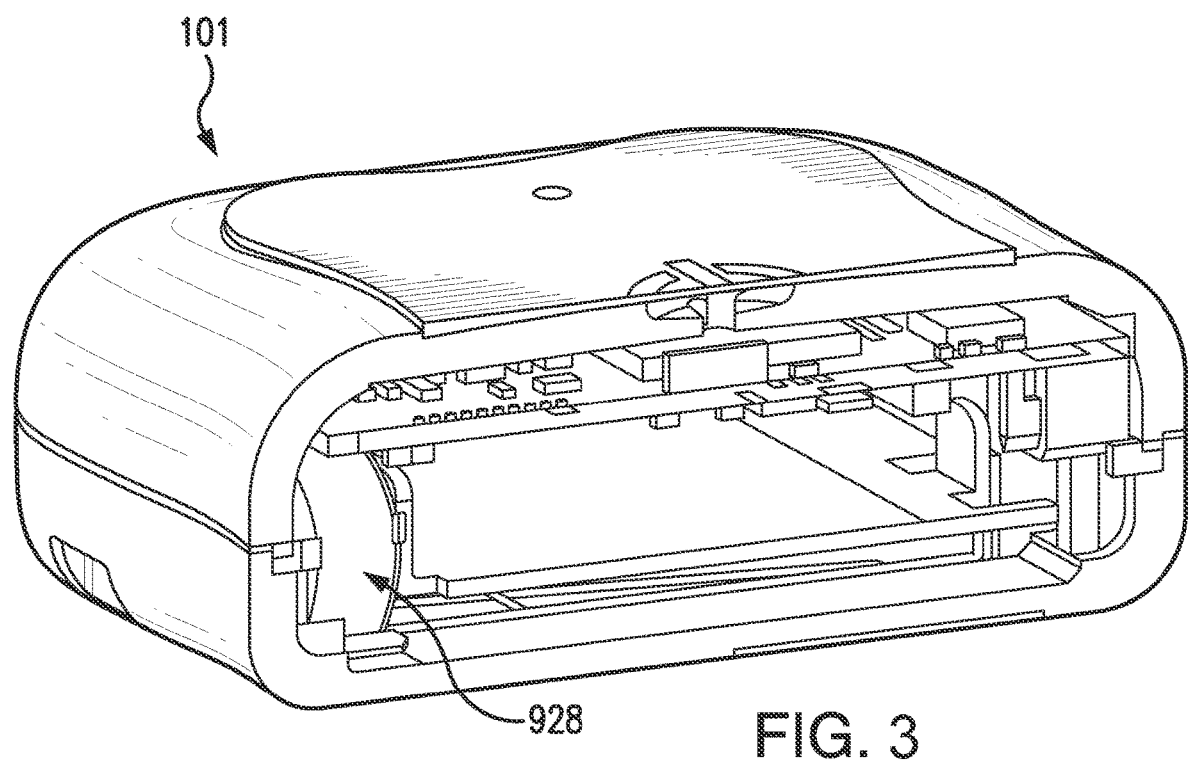
FIG. 3 illustrates a cross-sectional, perspective view of a transceiver embodying aspects of the invention.
Figure 4:
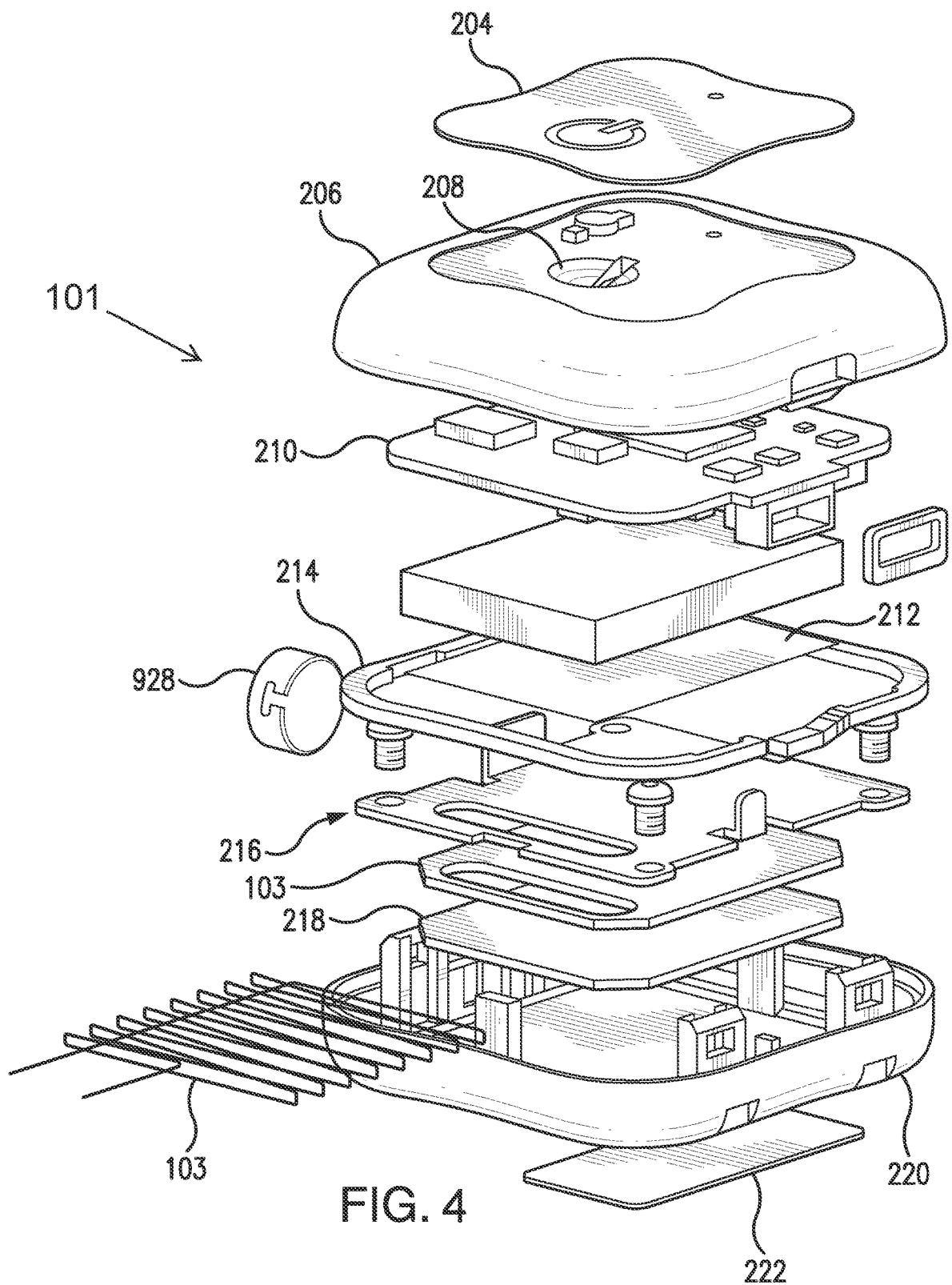
FIG. 4 illustrates an exploded, perspective view of a transceiver embodying aspects of the invention.

FIGS. 3 and 4 are cross-sectional and exploded views, respectively, of a non-limiting embodiment of the transceiver 101, which may be included in the analyte monitoring system illustrated in FIG. 1. As illustrated in FIG. 4, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
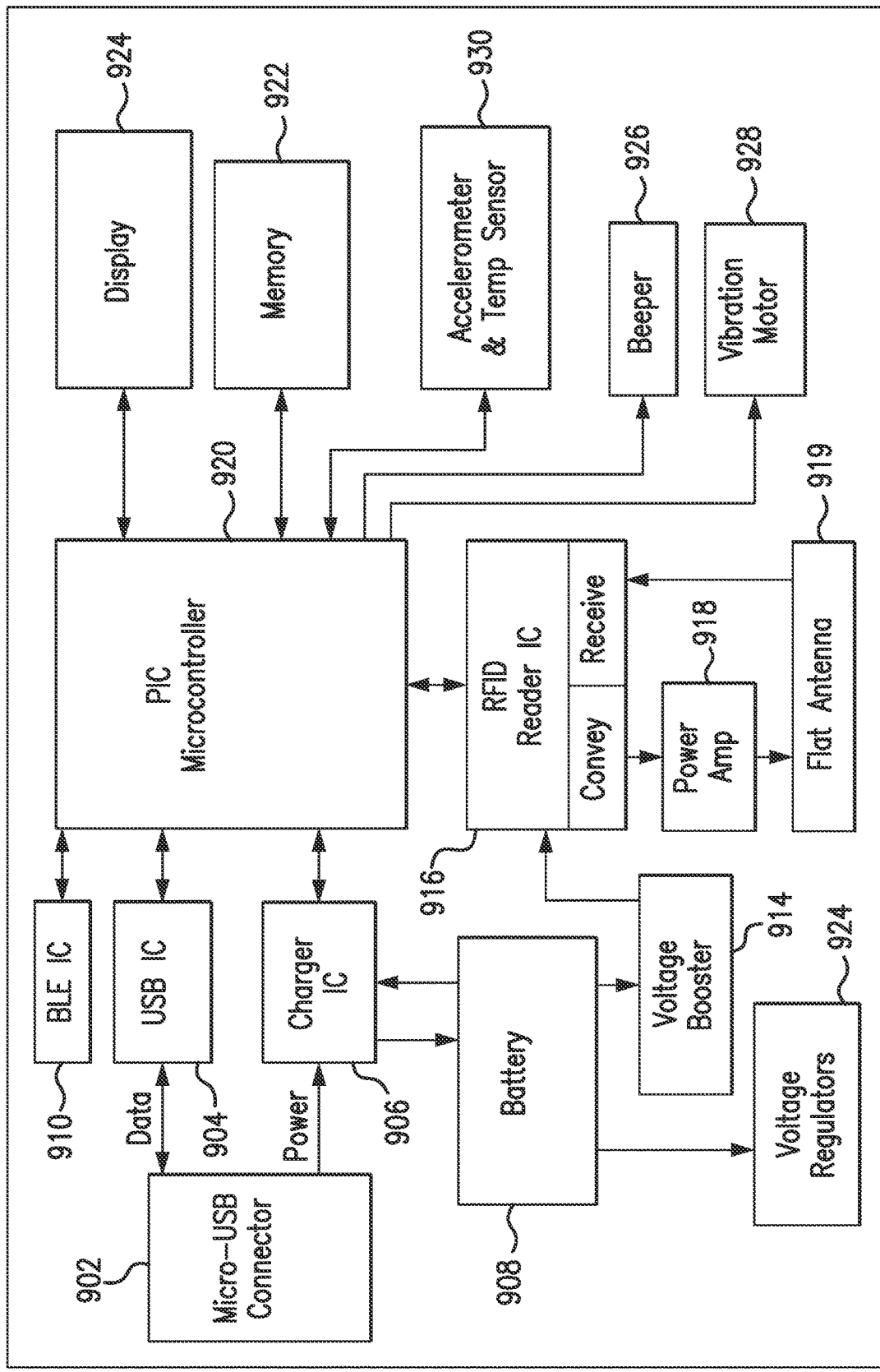
FIG. 5 illustrates a schematic view illustrating a transceiver embodying aspects of the present invention.

FIG. 5 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth™ standard, or a Bluetooth™ Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth™ antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to a radio-frequency identification (RFID) reader IC 916, which may use an inductor 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In some embodiments, as shown in FIG. 5, the inductor 103 may be a flat antenna 919. In some non-limiting embodiments, the inductor 103 may be flexible. However, as noted above, the inductor 103 of the transceiver 101 may be in any configuration that permits adequate field strength to be achieved when brought within adequate physical proximity to the inductor 114 of the sensor 100. In some embodiments, the transceiver 101 may include a power amplifier 918 to amplify the signal to be conveyed by the inductor 103 to the sensor 100.

In some embodiments, the transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductor 103. The PIC microcontroller 920 may also control processing of data received via the inductor 103, connector 902, or wireless communication IC 910.

In some embodiments, the transceiver 101 may include a sensor interface device, which may enable communication by the transceiver 101 with a sensor 100. In some embodiments, the sensor interface device may include the inductor 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a user interface including one or more of a display 924, a speaker 926, and a vibration motor 928. In some embodiments, the display device 924 may be a liquid crystal display and/or one or more light emitting diodes, and the PIC microcontroller 920 may control the display 924 to display data (e.g., analyte concentration values). In some embodiments, the speaker 926 (e.g., a beeper) and/or the vibration motor 928 may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC microcontroller 920.

In some embodiments, the transceiver 101 may be a body-worn transceiver that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transceiver's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by an application being executed by the display device 105. In other embodiments, the information from the transceiver 101 may be transmitted to a personal computer (PC) 109 or other secondary display devices (not shown) connected over a network.

In some embodiments, the transceiver 101 of the analyte monitoring system 50 may receive raw signals indicative of an amount or concentration of an analyte in proximity to the analyte indicator 106 of the analyte sensor 100. In some embodiments, the transceiver 101 may receive the raw signals from the sensor 100 periodically (e.g., every 5, 10, or 20 minutes). In some embodiments, the raw signals may include one or more measurements (e.g., one or more measurements indicative of the level of emission light 331 from the indicator molecules 104 as measured by the photodetector 224, one or more measurements indicative of the level of reference light 333 as measured by photodetector 226, and/or one or more temperature measurements as measured by the temperature transducer 670). In some embodiments, the transceiver 101 may use the received raw signals to calculate analyte concentration. In some embodiments, the transceiver 100 may store one or more calculated analyte concentrations (e.g., in memory 922). In some embodiments, the transceiver 100 may convey one or more calculated analyte concentrations to the display device 105, and the display device 105 may display the one or more calculated analyte concentrations.

In some embodiments, the analyte monitoring system 50 may calibrate the conversion of raw signals to analyte concentration. In some embodiments, the calibration may be performed approximately periodically (e.g., approximately every 12 or 24 hours). In some embodiments, the calibration may be performed using one or more reference measurements (e.g., one or more self-monitoring blood glucose (SMBG) measurements), which may be entered into the analyte monitoring system 50 using the user interface of the display device 105. In some embodiments, the transceiver 101 may receive the one or more reference measurements from the display device 105 and perform the calibration. One or more of the reference measurements may be erroneous and may lead to erroneous analyte measurement calculation if used as a calibration point for the calibrating of the conversion of raw sensor data to analyte measurements. Accordingly, the analyte monitoring system 5 (e.g., the transceiver 101) may determine whether to accept (or reject) reference measurements as calibration points in the calibration process. This calibration point acceptance process may be used to prevent erroneous reference measurements from being used as calibration points when calibrating the function used to convert raw sensor data (e.g., light and/or temperature measurements) into analyte measurements (e.g., analyte concentrations). In this way, the calibration point acceptance process may increase the accuracy and/or precision of the analyte measurements.

In some embodiments, the transceiver 101 may store the measurement information received from the sensor 100 (e.g., in memory 922). As noted above, the measurement information received from the sensor 100 may include one or more of: (i) a signal channel measurement with light source 108 on, (ii) a reference or second signal channel measurement with light source 108 on, (iii) a light source current source voltage measurement, (iv) field current measurement, (v) a diagnostic measurement, (vi) an ambient signal channel measurement with light source 108 off, (vii) an ambient reference or second signal channel measurement with light source 108 off, and (viii) a temperature measurement.

In some embodiments, the transceiver 101 may additionally store (e.g., in memory 922) other data with the measurement information received from the sensor 100. In some non-limiting embodiments, the other data may include one or more of: (i) an analyte concentration (e.g., in mg/dL, such as, for example, within a range of 20.0 to 400.0 mg/dL) calculated by the transceiver 101 from the measurement information, (ii) the date and time that the analyte measurement was taken, (iii) accelerometer values (e.g., x, y, and z) taken from an accelerometer of the transceiver 101 (e.g., an accelerometer of additional sensors 930), and/or (iv) the temperature of the transceiver 101 as measured by a temperature sensor of the transceiver 101 (e.g., a temperature sensor of additional sensors 930). In some embodiments, the transceiver 101 may keep track of the date and time and, as noted above, store the date and time along with the received analyte measurement information and/or calculated analyte concentration. In embodiments where the transceiver 101 includes an accelerometer, the accelerometer will enable tracking of activity levels of the subject that is wearing the transceiver 101. This activity level may be included in an event log and incorporated into various algorithms (e.g., for analyte concentration calculation, trending, and/or contributing to potential dosing levels for the subjects). In some embodiments, the transceiver 101 may store (e.g., in memory 922) any alert and/or alarm conditions detected based on the calculated analyte concentrations.

In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

Figure 6:
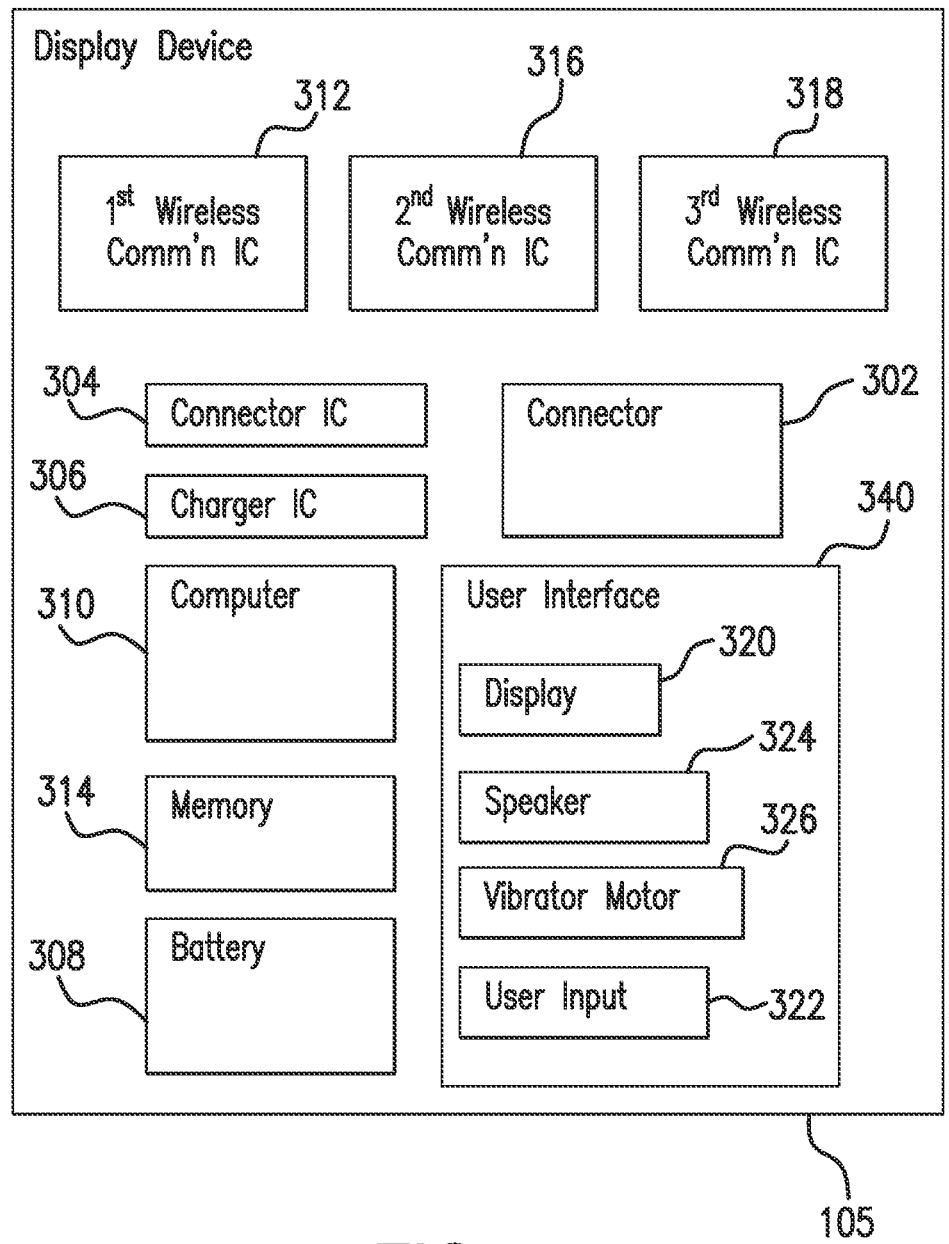
FIG. 6 illustrates a block diagram of a display device of the analyte monitoring system embodying aspects of the present invention.

FIG. 6 is a block diagram of a non-limiting embodiment of the display device 105 of the analyte monitoring system 50. As shown in FIG. 6, in some embodiments, the display device 105 may include one or more of a connector 302, a connector integrated circuit (IC) 304, a charger IC 306, a battery 308, a computer 310, a first wireless communication IC 312, a memory 314, a second wireless communication IC 316, a third wireless communication IC 318, and a user interface 340.

In some embodiments in which the display device 105 includes the connector 302, the connector 302 may be, for example and without limitation, a Micro-Universal Serial Bus (USB) connector. The connector 302 may enable a wired connection to an external device, such as a personal computer or transceiver 101. The display device 105 may exchange data to and from the external device through the connector 302 and/or may receive power through the connector 302. In some embodiments, the connector IC 304 may be, for example and without limitation, a USB-IC, which may control transmission and receipt of data through the connector 302.

In some embodiments in which the display device 105 includes the charger IC 306, the charger IC 306 may receive power via the connector 302 and charge the battery 308. In some non-limiting embodiments, the battery 308 may be, for example and without limitation, a lithium-polymer battery. In some embodiments, the battery 308 may be rechargeable, may have a short recharge duration, and/or may have a small size.

In some embodiments, the display device 105 may include one or more connectors and/or one or more connector ICs in addition to (or as an alternative to) connector 302 and connector IC 304. For example, in some alternative embodiments, the display device 105 may include a spring-based connector (e.g., Pogo pin connector) in addition to (or as an alternative to) connector 302, and the display device 105 may use a connection established via the spring-based connector for wired communication to a personal computer or the transceiver 101 and/or to receive power, which may be used, for example, to charge the battery 308.

In some embodiments in which the display device 105 includes the first wireless communication IC 312, the first wireless communication IC 312 may enable wireless communication with one or more external devices, such as, for example, one or more personal computers, one or more transceivers 101, and/or one or more other display devices 105. In some non-limiting embodiments, the first wireless communication IC 312 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the first wireless communication IC 312 may be configured to wirelessly transmit data at a frequency greater than 1 gigahertz (e.g., 2.4 or 5 GHz). In some embodiments, the first wireless communication IC 312 may include an antenna (e.g., a Bluetooth antenna). In some non-limiting embodiments, the antenna of the first wireless communication IC 312 may be entirely contained within a housing of the display device 105. However, this is not required, and, in alternative embodiments, all or a portion of the antenna of the first wireless communication IC 312 may be external to the display device housing.

In some embodiments, the display device 105 may include a transceiver interface device, which may enable communication by the display device 105 with one or more transceivers 101. In some embodiments, the transceiver interface device may include the antenna of the first wireless communication IC 312 and/or the connector 302. In some non-limiting embodiments, the transceiver interface device may additionally or alternatively include the first wireless communication IC 312 and/or the connector IC 304.

In some embodiments in which the display device 105 includes the second wireless communication IC 316, the second wireless communication IC 216 may enable the display device 105 to communicate with one or more remote devices (e.g., smartphones, servers, and/or personal computers) via wireless local area networks (e.g., Wi-Fi), cellular networks, and/or the Internet. In some non-limiting embodiments, the second wireless communication IC 316 may employ one or more wireless communication standards to wirelessly transmit data. In some embodiments, the second wireless communication IC 316 may include one or more antennas (e.g., a Wi-Fi antenna and/or one or more cellular antennas). In some non-limiting embodiments, the one or more antennas of the second wireless communication IC 316 may be entirely contained within a housing of the display device 105. However, this is not required, and, in alternative embodiments, all or a portion of the one or more antennas of the second wireless communication IC 316 may be external to the display device housing.

In some embodiments, in which the display device 105 includes the third wireless communication IC 318, the third wireless communication IC 318 may enable the display device 105 to communicate directly with the sensor 100 so that the display device 105 may additionally perform some or all of the functions of the transceiver 101. In some embodiments, the display device 105 and the sensor 100 may communicate using NFC (e.g. at a frequency of 13.56 MHz). In some embodiments, the display device 105 may include an inductor (e.g. flat antenna, loop antenna, etc.) that is configured to permit adequate field strength to be achieved when brought within adequate physical proximity to the inductor 114 of the sensor 100. In some non-limiting embodiments, the display device 105 may receive sensor data from the sensor 100 periodically (e.g., every 1, 2, 5, 10, 15, or 20 minutes). In some non-limiting embodiments, the display device 105 may receive sensor data from the sensor 100 on demand (e.g., when the display device 100 is hovered or swiped in proximity to the sensor 100). In some non-limiting embodiments, the display device 105 may include a sensor interface device, which may enable communication by the display device 105 with a sensor 100. In some embodiments, the sensor interface device may include the inductor. In some non-limiting embodiments, the sensor interface device may additionally include the RFID reader IC 916 and/or the power amplifier 918 described above with reference to FIG. 5.

In some embodiments in which the display device 105 includes the memory 314, the memory 314 may be non-volatile and/or capable of being electronically erased and/or rewritten. In some embodiments, the memory 314 may be, for example and without limitations a Flash memory.

In some embodiments in which the display device 105 includes the computer 310, the computer 310 may control the overall operation of the display device 105. For example, the computer 310 may control the connector IC 304, the first wireless communication IC 312, the second wireless communication IC 316, and/or the third wireless communication IC 318 to transmit data via wired or wireless communication. The computer 310 may additionally or alternatively control processing of received data (e.g., analyte monitoring data received from the transceiver 101).

In some embodiments in which the display device 105 includes the user interface 340, the user interface 340 may include one or more of a display 320 and a user input 322. In some embodiments, the display 320 may be a liquid crystal display (LCD) and/or light emitting diode (LED) display. In some non-limiting embodiments, the user input 322 may include one or more buttons, a keyboard, a keypad, and/or a touchscreen. In some embodiments, the computer 310 may control the display 320 to display data (e.g., analyte concentration values, analyte trend information, alerts, alarms, and/or notifications). In some embodiments, the user interface 340 may include one or more of a speaker 324 (e.g., a beeper) and a vibration motor 326, which may be activated, for example, in the event that a condition (e.g., a hypoglycemic or hyperglycemic condition) is met.

In some embodiments, the computer 310 may execute a mobile medical application (MMA). In some embodiments, the display device 105 may receive analyte monitoring data from the transceiver 101. The received analyte monitoring data may include one or more analyte concentrations, one or more analyte concentrations trends, and/or one or more sensor measurements. The received analyte monitoring data may additionally or alternatively include alarms, alerts, and/or notifications. In some embodiments, the display device 105 may receive measured analyte data directly from the sensor 100. The display device 105 may calculate an analyte concentration and an analyte concentration trend using at least the received sensor data. From this analyte information, the display device 105 may also determine if an alert and/or alarm condition exists, which may be signaled to the user (e.g., through vibration by a vibration motor and/or a display of a display device 105). In some embodiments, this analyte information (e.g., calculated analyte concentrations, calculated analyte concentration trends, alerts, alarms, and/or notifications) may be displayed by the MMA being executed by the display device 105. In some embodiments, the display device 105 may transmit this information (e.g., calculated analyte concentrations, calculated analyte concentration trends, alerts, alarms, and/or notifications) over a network such that a remote computing device (e.g., server) and one or more secondary display devices may receive, store, and display the analyte information.

In some embodiments, the analyte monitoring system 50 may calibrate the conversion of raw sensor measurements to analyte concentrations. In some embodiments, the calibration may be performed approximately periodically (e.g., every 12 or 24 hours). In some embodiments, the calibration may be performed using one or more reference measurements (e.g., one or more self-monitoring blood glucose (SMBG) measurements). In some embodiments, the reference measurements may be entered into the analyte monitoring system 50 using the user interface 340 of the display device 105. In some embodiments, the display device 105 may convey one or more references measurements to the transceiver 101, and the transceiver 101 may use the one or more received reference measurements to perform the calibration. In some embodiments, the display device may additionally or alternatively use the one or more reference measurements to perform a calibration.

Figure 7:
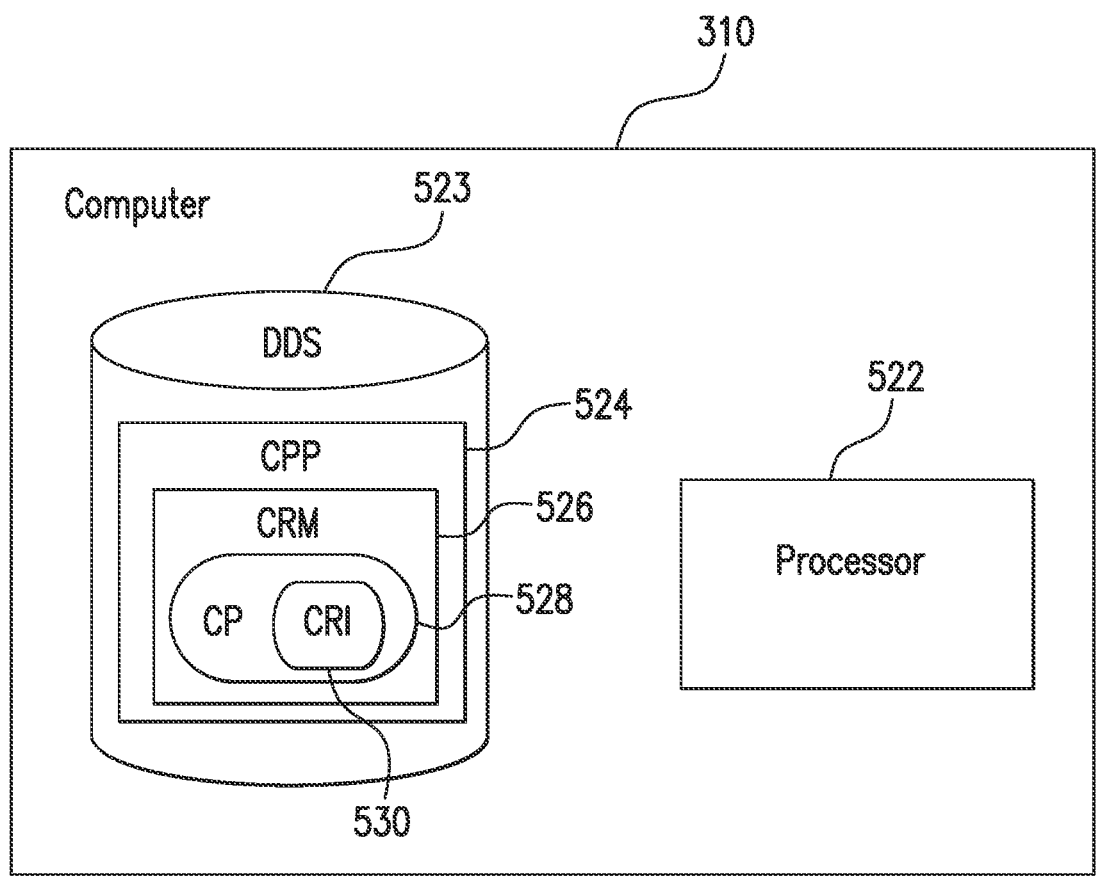
FIG. 7 illustrates a block diagram of a computer of the display device of the analyte monitoring system according to some embodiments.

FIG. 7 is a block diagram of a non-limiting embodiment of the computer 310 of the analyte monitoring system 50. As shown in FIG. 7, in some embodiments, the computer 310 may include one or more processors 522 (e.g., a general purpose microprocessor) and/or one or more circuits, such as an application specific integrated circuit (ASIC), field-programmable gate arrays (FPGAs), a logic circuit, and the like. In some embodiments, the computer 310 may include a data storage system (DSS) 523. The DSS 523 may include one or more non-volatile storage devices and/or one or more volatile storage devices (e.g., random access memory (RAM)). In embodiments where the computer 310 includes a processor 522, the DSS 523 may include a computer program product (CPP) 524. CPP 524 may include or be a computer readable medium (CRM) 526. The CRM 526 may store a computer program (CP) 528 comprising computer readable instructions (CRI) 530. In some embodiments, the CRM 526 may store, among other programs, the MMA, and the CRI 530 may include one or more instructions of the MMA. The CRM 526 may be a non-transitory computer readable medium, such as, but not limited, to magnetic media (e.g., a hard disk), optical media (e.g., a DVD), solid state devices (e.g., random access memory (RAM) or flash memory), and the like. In some embodiments, the CRI 530 of computer program 528 may be configured such that when executed by processor 522, the CRI 530 causes the computer 310 to perform steps described below (e.g., steps described below with reference to the MMA). In other embodiments, the computer 310 may be configured to perform steps described herein without the need for a computer program. That is, for example, the computer 310 may consist merely of one or more ASICs. Hence, the features of the embodiments described herein may be implemented in hardware and/or software.

In some embodiments in which the user interface 340 of the display device 105 includes the display 318, the MMA may cause the display device 105 to provide a series of graphical control elements or widgets in the user interface 340, such as a graphical user interface (GUI), shown on the display 318. The MMA may, for example without limitation, cause the display device 105 to display analyte related information in a GUI such as, but not limited to: one or more of analyte information, current analyte concentrations, past analyte concentrations, predicted analyte concentrations, user notifications, analyte status alerts and alarms, trend graphs, arrows, and user-entered events. In some embodiments, the MMA may provide one or more graphical control elements that may allow a user to manipulate aspects of the one or more display screens. Although aspects of the MMA are illustrated and described in the context of glucose monitoring system embodiments, this is not required, and, in some alternative embodiments, the MMA may be employed in other types of analyte monitoring systems.

In some embodiments where the display device 105 communicates with a transceiver 101, which in turn obtains sensor measurement data from the analyte sensor 100, the MMA may cause the display device 105 to receive and display one or more of glucose data, trends, graphs, alarms, and alerts from the transceiver 101. In some embodiments where the display device 105 communicates directly with the sensor 100 to obtain sensor measurement data, the MMA may cause the display device 105 to receive and display one or more of glucose data, trends, graphs, alarms, and alerts from the transceiver 101. In some embodiments, the MMA may store glucose level history and statistics for a patient on the display device 105 (e.g., in memory 314 and/or DSS 533) and/or in a remote data storage system.

In some embodiments, a user of the display device 105, which may be the same or different individual as patient, may initiate the download of the MMA from a central repository over a wireless cellular network or packet-switched network, such as the Internet. Different versions of the MMA may be provided to work with different commercial operating systems, such as the Android OS or Apple OS running on commercial smart phones, tablets, and the like. For example, where display device 105 is an Apple iPhone, the user may cause the display device 105 to access the Apple iTunes store to download a MMA compatible with the Apple OS, whereas where the display device 105 is an Android mobile device, the user may cause the display device 105 to access the Android App Store to download a MMA compatible with the Android OS.

Figure 8:
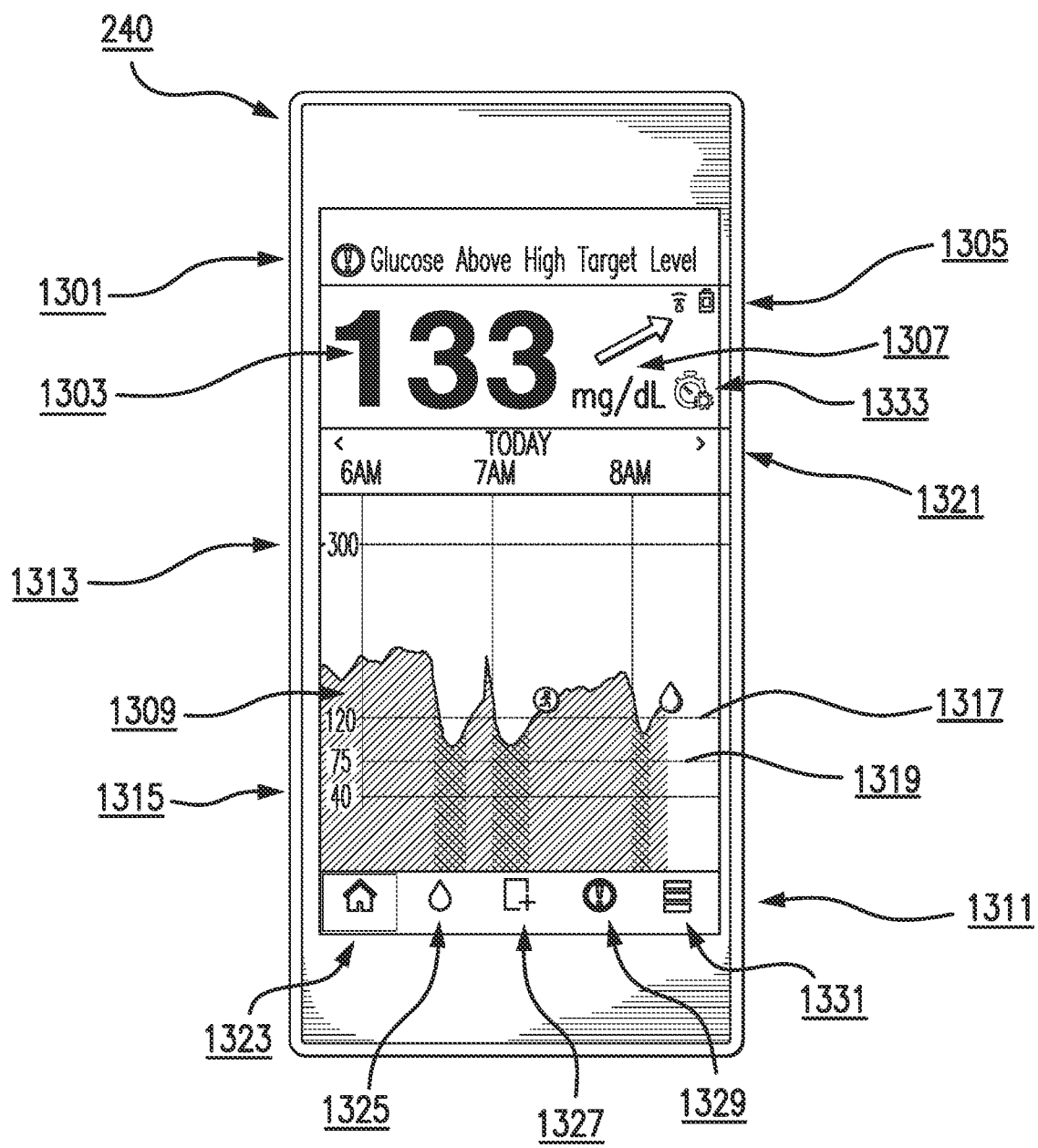
FIG. 8 illustrates a non-limiting example of a home screen illustrative display of a medical mobile application embodying aspects of various embodiments of the present invention.

FIG. 8 is an example of a home screen display of a medical mobile application (MMA) in accordance with aspects of various embodiments of the present invention. According to some embodiments, the workspace display of the MMA may be depicted in a GUI on the display 320 of the display device 105. In some embodiments, the home screen may display one or more of real-time analyte concentrations either received from transceiver 101 or calculated by the display device 105, rate and direction of analyte level change, graphical trends of analyte levels, alarms or alerts for hypoglycemia or hyperglycemia, and logged events such as, for example and without limitation, meals, exercise, and medications. Table 1 below depicts several informational non-limiting examples of items and features that may be depicted on the home screen.

TABLE 1

| Home Screen | |
|---|---|
| Status bar | Shows the status of user's glucose level |
| Transceiver/Transmitter ID | This is the transceiver being used; the transceiver name can be changed by going to Settings > System |
| Current glucose value | A real-time glucose reading; this may be updated every 5 minutes |
| Date and time | The current date and time with navigational options, such as scroll left or right to see different dates and times |
| Alarm and Events | Shows an icon when an alert, alarm, or event occurs |
| Bluetooth Connection | Shows the strength of the Bluetooth connection |
| Handheld Device Battery Level | Indicates the battery strength of the handheld device |
| Transmitter/Transceiver Battery Level | Indicates the battery strength of the transceiver |
| Transmitter/Transceiver Connection Status Icon | Shows the strength of the transceiver connection |
| Trend Arrow | Shows the direction a patient's glucose level is trending |
| Unit of Measurement | This is the units for the glucose value |

TABLE 1-continued

| Home Screen | |
| --- | --- |
| High Glucose Alarm Level | This is the high glucose alarm or alert level set by a user |
| Glucose High Target Level | This is the high glucose target level set by a user |
| Stacked Alerts | Shows when there are several alerts at the same time |
| Glucose Trend Graph | A user can navigate or scroll through the graph to see the trend over time |
| Menu | Navigation to various sections of the MMA, such as:<br>Home  Reports  Settings<br>Calibrate  Share My Data  About<br>Notifications  Placement Guide<br>Event Log  Connect |
| Calibration Point Icon | This icon appears when a calibration is entered |
| Profile Indicator | This indicator may indicate what profile is being applied, such as a normal profile, temporary profile, vacation profile, and the like. |

In some embodiments, as shown in FIG. 8, the home screen may include one or more of a status notification bar 1301, a real-time current glucose level 1303 of a patient, one or more icons 1305, a trend arrow 1307, a historical graph 1309, a profile indicator 1333, and navigation tools 1311. The status notification bar 1301 may depict, for example and without limitation, alarms, alerts, and notifications related to, for example, glucose levels and system statistics and/or status. The one or more icons 1305 may represent the signal strength of the transceiver 101 and/or the battery level of the transceiver 101. The trend arrow 1307 may indicate a rate and/or direction of change in glucose measurements of a patient. The historical graph may be, for example and without limitation, a line graph and may indicate trends of glucose measurement levels of a patient. The navigation tools 1311 may allow a user to navigate through different areas or screens of the MMA. The screens may include, for example and without limitation, one or more of Home, Calibrate, Event Log, Notifications, and Menu screens.

In some embodiments, the historical graph 1309 may depict logged events and/or user inputted activities such as meals (nutrition, amount of carbohydrates), exercise (amount of exercise), medication (amount of insulin units), and blood glucose values as icons on positions of the graph corresponding to when such events occurred. In some embodiments, the historical graph 1309 may show one or more of a boundary or indication of a high glucose alarm level 1313, a low glucose alarm level 1315, a high glucose target level 1317, and a low glucose target level 1319. In some embodiments, a user may interact with a time or date range 1321 option via the GUI to adjust the time period of the glucose level displayed on the historical graph 1309. In some embodiments, the date range 1321 may be specified by a user and may bet set to different time periods such as 1, 3, 24 hours, 1, 7, 14, 30, and 60 days, weeks, months, etc. In some embodiments, the line graph 1309 may show high, low, and average glucose levels of a patient for the selected date range 1321. In other embodiments, the line graph 1309 may be a pie chart, log book, modal day, or other depiction of glucose levels of a patient over a selectable date range 1321, any of which may further depict high, low, and average glucose levels of the patient over that date range 1321.

In some non-limiting embodiments, the trend arrow 1307 may be depicted in five different configurations that signify direction (up, down, neutral) and rate (rapidly, very rapidly slow, slow, very slow, and stable) of glucose change. In some non-limiting embodiments, the MMA and/or the transceiver 101 may use the last twenty minutes of continuous glucose measurement data received from the sensor 101 and/or processed by the transceiver 730 in the calculation used to determine the orientation of the trend arrow 1307. In some embodiments, there may be times when the trend arrow 1307 may not be displayed due to, for example, there being insufficient sensor values available for the trend calculation. In some embodiments, a trend arrow 1307 displayed in a horizontal orientation (approximately 0° along the horizontal direction of the GUI display) may indicate that the glucose level is changing gradually, such as, for example, at a rate between −1.0 mg/dL and 1.0 mg/dL per minute. In some embodiments, a trend arrow 1307 displayed slightly in the upwards direction (approximately 45° up from the horizontal direction of the GUI display) may indicate that the glucose level is rising moderately, such as, for example, at a rate between 1.0 mg/dL and 2.0 mg/dL per minute. In some embodiments, a trend arrow 1307 displayed slightly in the downwards direction (approximately 45° down from the horizontal direction of the GUI display) may indicate that the glucose level is falling moderately, such as, for example, at a rate between 1.0 mg/dL and 2.0 mg/dL per minute. In some embodiments, a trend arrow 1307 displayed in a vertical direction (approximately 90° up from the horizontal direction of the GUI display) may indicate that the glucose level is rising very rapidly, such as, for example, at a rate more than 2.0 mg/dL per minute. In some embodiments, a trend arrow 1307 displayed in a downwards direction (approximately 90° down from the horizontal direction of the GUI display) may indicate that the glucose level is falling very rapidly, such as, for example, at a rate more than 2.0 mg/dL per minute. In some embodiments, the trend arrow 1307 is different from a predicted glucose alarm or alert. For example, the trend arrow 1307 may indicate rate and direction of change regardless of glucose value, whereas predicted glucose alarms or alerts may indicate reaching a certain glucose level based on current trends. For example, the MMA may cause a predicted low glucose alarm or alert to be displayed in the notification bar 1301 while still displaying a relatively stable trend arrow 1307 (e.g., at 0° or 45° from the horizontal direction of the GUI display).

In some embodiments, the historical line graph 1309 may allow user to quickly review and analyze historical data and/or trend information of a patient's glucose levels over time. In some embodiments, the historical line graph 1309 may include icons or markers along the trend line to reflect alarms, alerts, notifications, and/or any events that were automatically or manually logged by the user into the display device 105 via a GUI display generated by the MMA. Where one or more of such icons or markers are displayed on the historical line graph 1309, a user may select any one of the icons or markers to obtain more information about the item. For example, in response to a selection of a mark on the line graph 1309, the MMA may generate a popup window on the display 220 that provides more information about the mark.

In some embodiments, the historical line graph 1309 may enable a user to quickly review how well a patient is doing against glucose targets and/or alarms or alerts. For example, a user may establish a high glucose alarm level 1313 and/or a low glucose alarm level 1315, as well as a high glucose target level 1317 and/or a low glucose target level 1319. The high glucose alarm level 1313 and/or low glucose alarm level 1315 may be visually depicted over the historical line graph 1309, for example, using a colored dashed line (such as red). Additionally, the high glucose target level 1317 and low glucose target level 1319 may be visually depicted over the historical line graph 1309, for example, using a color dashed line (such as green).

In some embodiments, the colors of the historical line graph 1309 may change depending on a glucose level 1303 status. For example, during the times where the glucose level 1303 was outside of the high glucose alarm level 1313 or low glucose alarm level 1315, then the portion of the line graph 1309 corresponding to those times may be filled in red. As another example, during the times where the glucose level 1303 is between the high glucose target level 1317 and the low glucose target level 1319, then the portion of the line graph 1309 corresponding to those times may be filled in green. As yet another example, during the times where the glucose level 1303 is between a glucose target level 1317, 1319 and a corresponding alarm level 1313, 1315, then the portion of the line graph 1309 may be filled in yellow.

In some embodiments, the line graph 1309 may be displayed with one or more selectable date range icons 1321 that allow a user to change the day/time period corresponding to the line graph 1309 in real-time. For example, a user may select a forwards or backwards selectable option (such as an arrow) or use a swipe or fling gesture that may be recognized by GUI to navigate to a later or earlier time period, respectively, such as a day, month, etc. In some embodiments a user may choose an older graph 1309 to display by tapping the date on the date range 1321 portion of the screen and submitting or entering a desired date and/or time to review. In some embodiments, a user may use one or more gestures that are recognized by the GUI, such as a pinch, zoom, tap, press and hold, or swipe, on graph 1309. For example, a user may pinch the historical line graph 1309 with a thumb and index finger in order to cause the MMA to display different time/dating settings or adjust a time/date setting on the line graph 1309. In some embodiments, a user may tap or press and hold a time event on historical line graph 1309, and in response the MMA may display further detail on the time event, such as a history, reading value, date/time, or association to other events or display a prompt for entry of a time event.

In some embodiments, the MMA may store glucose data 1303 on the display device 105 (e.g., in memory 214 and/or DSS 533) so long as there is available memory space. Additionally or alternatively, the MMA may cause the display device 105 to send a sync request message to store the glucose data 1303 on a remote storage device.

In some embodiments, the MMA may cause the GUI to display navigational tools 1311 that allow a user to navigate to different features and screens provided by the MMA. For example, the navigational tools 1311 may include a navigation bar with one or more of a plurality of selectable navigation options 1323, 1325, 1327, 1329, and 1331, such as buttons or icons. As shown in FIG. 4, in some embodiments, the selectable navigation options may allow a user to navigate to one or more of the "Home" screen 1323, a "Calibrate" screen 1325, an "Event Log" screen 1327, a "Notifications" screen 1329, and a "Menu" screen 1331. Upon a user selection of one of the selectable navigation options in the navigation tools area 1311, a new screen corresponding to the selected option may be displayed on a display device by the GU In some embodiments where the system includes the data management system (DMS) 111 (see FIG. 1), the DMS 111 may be a web-based analyte DMS. In some embodiments, the DMS 111 may be a server device employed to allow data to be shared over the network such as the Internet. The server may share data via proprietary formats configured to be employed by hardware computing systems configured, at least in part, with applications to make the hardware computing system into an analyte monitoring system. In some embodiments, data from the display device 105 and/or PC 109 may be uploaded (e.g., through a wired connection such as, for example, a USB connection or a wireless connection such as, for example, a wireless Internet connection) to a web server on a remote computer. In some embodiments, the DMS 111 may enable sharing of the analyte data (e.g., allowing the user, caregiver, and/or clinician to view sensor analyte data). The user may collect analyte data at home or in a clinic/research facility and then upload the data to their computer web account. Using the web account, the DMS 111 may use the data to generate one or more different reports utilizing the uploaded information. For example, in some non-limiting embodiments, the DMS 111 may use the uploaded data to generate one or more of the following reports: (i) an analyte details report, (ii) an analyte line report, (iii) a modal day report, (iv) a modal summary report, (v) a statistics report, and (vi) a transceiver log report.

In some embodiments, a user may use the DMS 111 to register with the DMS 111 and create a unique user ID and password. Once logged in, the user may enter their basic user information and may upload analyte reading data from their transceiver 101 or display device 105. In various embodiments, the DMS 111 may support specific data types such as, for example, glucose, insulin, meal/carbs, exercise, health event, alarms, and errors. In some non-limiting embodiments, data can be automatically uploaded or entered manually by the user or imported from the transceiver 101 and then saved in the DMS 111 to be viewed at a later date.

In some embodiments, the analyte monitor system 50 may be used according to two or more modes including (i) a continuous glucose monitoring (CGM) mode and (ii) a flash glucose monitoring (FGM) mode. In some embodiments, a host or user of the analyte sensor 100 may switch back and forth between using the analyte monitor system 50 according to the the CGM mode and using the analyte monitor system 50 in the FGM mode. In some embodiments, the host or user may use the analyte monitoring system 50 according to the CGM mode by placing the transceiver 101 in proximity to the analyte sensor 100 (e.g., using adhesive or an armband) so that the transceiver 101 and analyte sensor can communicate. In some embodiments, the host or user may use the analyte monitoring system 50 according to the FGM mode by using the display device 105 to communicate directly with the analyte sensor 100. In some embodiments, when a host or user is using the analyte monitoring system 50 according to the CGM mode, the transceiver 101 may cause the analyte sensor 100 to take one or more measurements and convey the sensor data directly to the transceiver 101. In some non-limiting embodiments, when the analyte monitoring system 50 is being used according to the CGM mode, the transceiver 101 may cause the analyte sensor 100 to convey sensor data on a periodic basis (e.g., every five minutes, ten minutes, or fifteen minutes). In some embodiments, when a host or user is using the analyte monitoring system 50 according the FGM mode, the display device 105 may cause the analyte sensor 100 to take one or more measurements and convey the sensor data directly to the display device 105. In some non-limiting embodiments, when the analyte monitoring system 50 is being used according to the FGM mode, the display device 105 cause the analyte sensor 100 to convey sensor data on demand (e.g., by hovering or swiping the display device 105 in proximity to the analyte sensor 100).

In some embodiments, while the analyte monitor system 50 is being used according to the CGM mode, the transceiver 101 may be operatively linked to the sensor 100. In some embodiments, under the CGM mode, the transceiver 101 may be placed within adequate physical proximity to the sensor 100 using an adhesive patch, strap, or belt, such that the transceiver 101 is worn on a body of a host. In some embodiments, under the CGM mode, the transceiver 101 may supply power to the sensor 100 and receive sensor measurement data (e.g., raw signals indicative of an amount or concentration of glucose) from the sensor 100. In some embodiments, under the CGM mode, the transceiver 101 may periodically use the received sensor measurement data to calculate analyte information, such as for example, one or more analyte concentrations and an analyte concentration trend. In some embodiments, under the CGM mode, the transceiver 101 may also determine if an alert and/or alarm condition exists based on the calculated analyte concentrations and analyte concentration trends. In some embodiments, the transceiver 101 may display the analyte concentrations, the analyte concentration trend, the alert, or the alarm on the display 924 of the transceiver 101. In some embodiments, the transceiver 101 may notify the user or host about the alert and/or alarm by generating sound with the speaker 926 of the transceiver and/or generating vibration with the vibration motor 928 of the transceiver.

In some embodiments, under the CGM mode, the display device 105 may use the first wireless communication IC 312 to communicate with the transceiver 101 (e.g., via Bluetooth™ Low Energy with Advanced Encryption Standard (AES)-Counter CBC-MAC (CCM) encryption). In some embodiments, the display device 105 may use the first wireless communication IC 312 to receive information from the transceiver 101 (e.g., calculated analyte concentrations, calculated analyte concentration trends, alerts, alarms, and/or notifications). In some embodiments, under the CGM mode, the display device 105 may additionally receive sensor data, which was received by the transceiver 101 from the analyte sensor 100. In some non-limiting embodiments, under the CGM mode, the transceiver 101 may calculate analyte information using at least the sensor data received directly from the analyte sensor 100, and the display device 105 may also calculate analyte information using the sensor data received indirectly from the analyte sensor 100 via the transceiver 101. However, this is not required, and, in some embodiments, only the transceiver 101 calculates analyte information using the sensor data.

In some alternative embodiments, under the CGM mode, only the display device 105 calculates analyte information using sensor data received indirectly from the analyte sensor 100 via the transceiver 101. In some alternative embodiments, under the CGM mode, the transceiver 101 may convey sensor data received from the analyte sensor 100 to the display device 105 without calculating any analyte information using the sensor data. That is, in some embodiments, under the CGM mode, only the display device 105 (and not the transceiver 101) calculates analyte information using the sensor data received from the transceiver 101.

In some embodiments, while the analyte monitor system 50 is being used according to the FGM mode, the display device 105 may be used to communicate directly with the sensor 100. In some embodiments, under the FGM mode, the display device 105 may use the third wireless communication IC 318 to communicate directly with the sensor (e.g., via NFC at a frequency of 13.56 MHz) and cause the analyte sensor 100 to convey sensor measurement data (e.g., raw signals indicative of an amount or concentration of glucose) to the display device 105. In some embodiments, under the FGM mode, the display device 105 may cause the analyte sensor 100 to convey sensor measurement data on-demand by positioning (e.g., hovering or swiping) the display device 105 within physical proximity to the sensor 100. In some embodiments, the positioning the display device 105 in proximity to the analyte sensor 100 may provide adequate coupling between the inductor 114 of the sensor 100 and an inductor of the display device 105. In some embodiments, the display device 105 may supply power to the sensor 100 when the display device 105 is brought in proximity to the sensor 100. However, it is not required that the display device 105 supply power to the sensor 100, and, in some alternative embodiments, the display device 105 may not do so.

In some embodiments, the analyte sensor 100 may be a passive device configured to take measurements only when the transceiver 101 or display device 105 triggers sensor measurements. In some alternative embodiments, the analyte sensor 100 may include a charge storage device (not shown), such as, for example and without limitation, a battery, supercapacitor, or ultracapacitor, that stores a sufficient amount of energy to maintain the sensor 100 in an operating state even when not operatively linked to either of the transceiver 101 and the display device 105. The charge storage device may allow the analyte sensor to obtain measurements autonomously (e.g., on a periodic basis). Accordingly, in some embodiments, when the transceiver 101 or display device 101 causes the analyte sensor 100 to convey sensor measurements, the analyte sensor 100 may convey one or more current measurements and/or one or more previous measurements taken by the sensor 100 autonomously.

In some embodiments, under the FGM mode, the display device 105 may use sensor measurement data received directly from the analyte sensor 100 to calculate analyte information, such as for example and without limitation, one or more analyte concentrations and an analyte concentration trend. In some embodiments, the display device 105 may determine whether an alert and/or alarm condition exists based on the calculated analyte concentrations and/or analyte concentration trends.

In some embodiments, while using the analyte monitoring system 50 according to the FGM mode, the transceiver 101 may be operatively disconnected from the sensor 100 such that the transceiver 101 is not within physical proximity to the sensor 100. In some embodiments, while using the analyte monitoring system 50 according to the FGM mode, the transceiver 101 may not be worn on the body of the host or user of the analyte monitor system 50. In some embodiments, the display device 105 may be configured to generate a reminder notice to the user or host to cause the analyte sensor 100 to convey sensor data to the display device 105 if the display device 105 has not received sensor data for a predetermined period of time.

In some embodiments, the MMA executed by the display device 105 may cause the display device 105 to display the analyte information (e.g., calculated analyte concentrations, calculated analyte concentration trends, alerts, alarms, and/or notifications). In some embodiments, the display device 105 may display both (i) analyte information generated when the analyte monitoring system 50 is used according to the CGM mode and (ii) analyte information generated when the analyte monitoring system 50 is used according to the FGM mode. In some embodiments, the display device 105 may display (i) analyte information calculated by and received from the transceiver 101 and (ii) analyte information calculated by the display device 105 using at least sensor data received directly from the analyte sensor 100. In some alternative embodiments, the display device 105 may display (i) analyte information calculated by the display device 105 using at least sensor data received indirectly from the analyte sensor 100 via the transceiver 101 and (ii) analyte information calculated by the display device 105 using at least sensor data received directly from the analyte sensor 100. In some embodiments, the display device 105 may transmit analyte information (e.g., calculated analyte concentrations, calculated analyte concentration trends, alerts, alarms, and/or notifications) over a network such that a remote computing device (e.g., server) and one or more secondary display devices may receive, store, and display the analyte information.

In some embodiments, while using the analyte monitoring system 50 according to the FGM mode, the transceiver 101 may be operatively disconnected from the sensor 100 such that the transceiver 101 is not within physical proximity to the sensor 100. In some embodiments, while using the analyte monitoring system 50 according to the FGM mode, the transceiver 101 may not be worn on the body of the host or user of the analyte monitor system 50. In some embodiments, under the FGM mode, the MMA application is configured to generate a reminder notice to the user or host to cause the analyte sensor 100 to convey sensor data to the display device 105 if the display device 105 has not received sensor data for a predetermined period of time.

Figure 9:
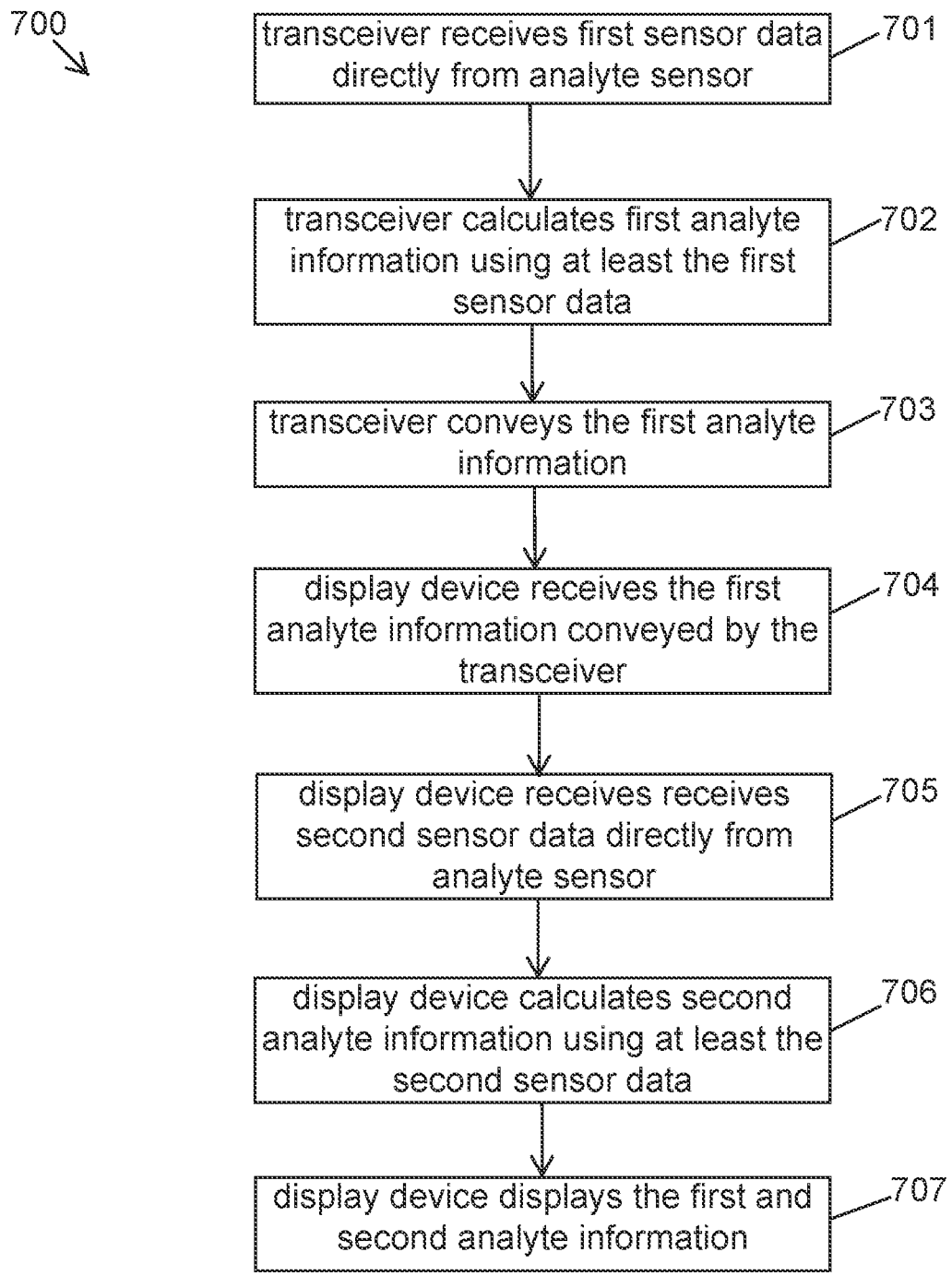
FIG. 9 is a flow chart illustrating a method of using an analyte monitoring system embodying aspects of the present invention.

FIG. 9 is a flow chart illustrating a process 700 embodying aspects of the present invention. In some embodiments, the process 700 may include one or more steps (e.g., steps 701-703) in which the analyte monitoring system 50 is used according to the CGM mode and one or more steps (e.g., steps 704-705) in which the analyte monitoring system 50 is used according to the FGM mode.

In some embodiments, the process 700 may include a step 701 in which a transceiver 101 receives first sensor data directly from an analyte sensor 100. In some non-limiting embodiments, in step 701, the transceiver 101 may cause the sensor to take one or more measurements and convey the first sensor data to the transceiver 101 (e.g., by conveying one or more measurement commands to the analyte sensor 100). In some embodiments, during step 701, the transceiver 101 may have been positioned such that the transceiver 101 is operatively linked to the analyte sensor 100. In some embodiments, the transceiver 101 may have been positioned to be operatively linked to the analyte sensor 100 by wearing the transceiver 101 on an armband, a wrist band, a waist band, or an adhesive patch. In some embodiments, the transceiver 101 may use the inductor 103 and RFID reader IC 916 to receive the second sensor data directly from the analyte sensor 100. In some embodiments, the transceiver 101 may receive the first sensor data from the analyte sensor 100 wirelessly using a communication standard such as, for example and without limitation, an NFC standard. In some non-limiting embodiments, the analyte sensor 101 may convey the first sensor data by modulating an electromagnetic wave generated by the transceiver 101, and the transceiver 101 receiving the first sensor data may include detecting the modulations. In some non-limiting embodiments, the analyte sensor 100 may use the electromagnetic wave to power the analyte sensor 100. In some embodiments, the first sensor data may include one or more raw measurements (e.g., one or more light measurements and one or more temperature measurements).

In some embodiments, the process 700 may include a step 702 in which the transceiver 101 calculates first analyte information using at least the received first sensor data. In some embodiments, the calculated first analyte information may include one or more of an analyte concentration and an analyte concentration trend. In some embodiments, the step 702 of calculating the first analyte information may include determining if an alert and/or alarm condition exists based on at least the calculated first analyte information (e.g., an analyte concentration and/or analyte concentration trend). In some embodiments, the alert and/or alarm conditions may include one or more of a high analyte alarm level, a low analyte alarm level, a high target analyte level, and a low target analyte level.

In some embodiments, the process 700 may include a step 703 in which the transceiver 101 conveys the first analyte information. In some embodiments, the first analyte information may be conveyed wirelessly. In some embodiments, the transceiver 101 may convey the first analyte information using the wireless communication IC 910. In some embodiments, the transceiver 101 may employ a communication standard (e.g., a Bluetooth™ LE standard) to convey the first analyte information. In some alternative embodiments, the first analyte information may be conveyed using a wired connection (e.g., using a wired connection between the connector 902 of the transceiver 101 and the connector 30 of the display device 105).

In some embodiments, the process 700 may include a step 704 in which the display device 105 receives the first analyte information conveyed by the transceiver 101. In some embodiments, the display device 105 may use the first wireless communication IC 312 to receive the first analyte information conveyed by the transceiver 101.

In some embodiments, the process 700 may include a step 705 in which the display device 105 receives second sensor data directly from the analyte sensor 100. In some non-limiting embodiments, in step 704, the display device 105 may cause the sensor 100 to take one or more measurements and convey the second sensor data to the display device 105 (e.g., by conveying one or more measurement commands to the analyte sensor 100). In some embodiments, during step 705, the display device 105 may have been positioned such that the display device 105 is operatively linked to the analyte sensor 100. In some embodiments, the display device 105 may be operatively linked to the analyte sensor 100 by positioning the display device 105 in proximity to the analyte sensor 100 (e.g., by hovering or swiping the display device 105 in proximity to the analyte sensor 100). In some non-limiting embodiments, during step 705, the transceiver 101 is not positioned in proximity to the analyte sensor 100, and/or the transceiver 101 is not operatively linked to the analyte sensor 100. In some embodiments, the display device 105 may use the third wireless communication IC 318 to receive the second sensor data directly from the analyte sensor 100. In some embodiments, the display device 105 may receive the second sensor data from the analyte sensor 100 wirelessly using a communication standard such as, for example and without limitation, an NFC standard. In some non-limiting embodiments, the analyte sensor 101 may convey the second sensor data by modulating an electromagnetic wave generated by the display device 105, and the display device 105 receiving the second sensor data may include detecting the modulations. In some non-limiting embodiments, the analyte sensor 100 may use the electromagnetic wave to power the analyte sensor 100. In some embodiments, the second sensor data may include one or more raw measurements (e.g., one or more light measurements and one or more temperature measurements).

In some embodiments, the process 700 may include a step 706 in which the display device 105 calculates second analyte information using at least the second sensor data. In some embodiments, the calculated second analyte information may include calculating one or more of an analyte concentration and an analyte concentration trend. In some embodiments, step 706 may include the display device 105 determining whether an alert and/or alarm condition exists based on the second analyte information (e.g., a calculated analyte concentration and/or analyte concentration trend). In some embodiments, the alert and/or alarm conditions may include one or more of a high analyte alarm level, a low analyte alarm level, a high target analyte level, and a low target analyte level.

In some embodiments, the process 700 may include a step 707 in which the display device 105 displays the first analyte information and the second analyte information. In some embodiments, the MMA being executed by the computer 310 of the display device 105 may cause the user interface 340 of the display device 105 to display the first and second analyte information. For example, in some embodiments, the display device 105 may display the first analyte information after it is received from the transceiver 101 and then additionally display the second analyte information after it is calculated by the display device 105. In some embodiments, step 707 may include displaying one or more of glucose data, trends, graphs, alarms, and alerts.

In some embodiments, the process 700 may include an additional step in which the display device 105 may convey the first analyte information and the second analyte information over a network to a remote device. In some embodiments, the step of conveying the first analyte information and the second analyte information may include the display device 105 using the second wireless communication IC 316 to transmit the first and second sets of analyte information via network, such as for example and without limitation, a wireless local area network (e.g., Wi-Fi), a cellular network, and/or the Internet.

While the process 700 described above is shown in a sequence of steps, it should be understood that the sequence of steps may be altered, additional steps may be added, and some steps may be omitted without departing from the scope of the present disclosure. For example, in some alternative embodiments, steps 705 and 706 may be performed before steps 701-704. For another example, in some embodiments, process 700 may include additional steps in which the transceiver 101 receives third sensor data from the analyte sensor 100, the transceiver 101 calculates third analyte information using at least the third sensor data, the transceiver 101 conveys the third analyte information to the display device, and the display device 105 displays the first, second, and third analyte information. For yet another example, the process 700 may include additional steps in which the display device 105, receives fourth sensor data directly from the analyte sensor 100, calculates fourth analyte information, and displays at least the first, second, and fourth analyte information.

Figure 10:
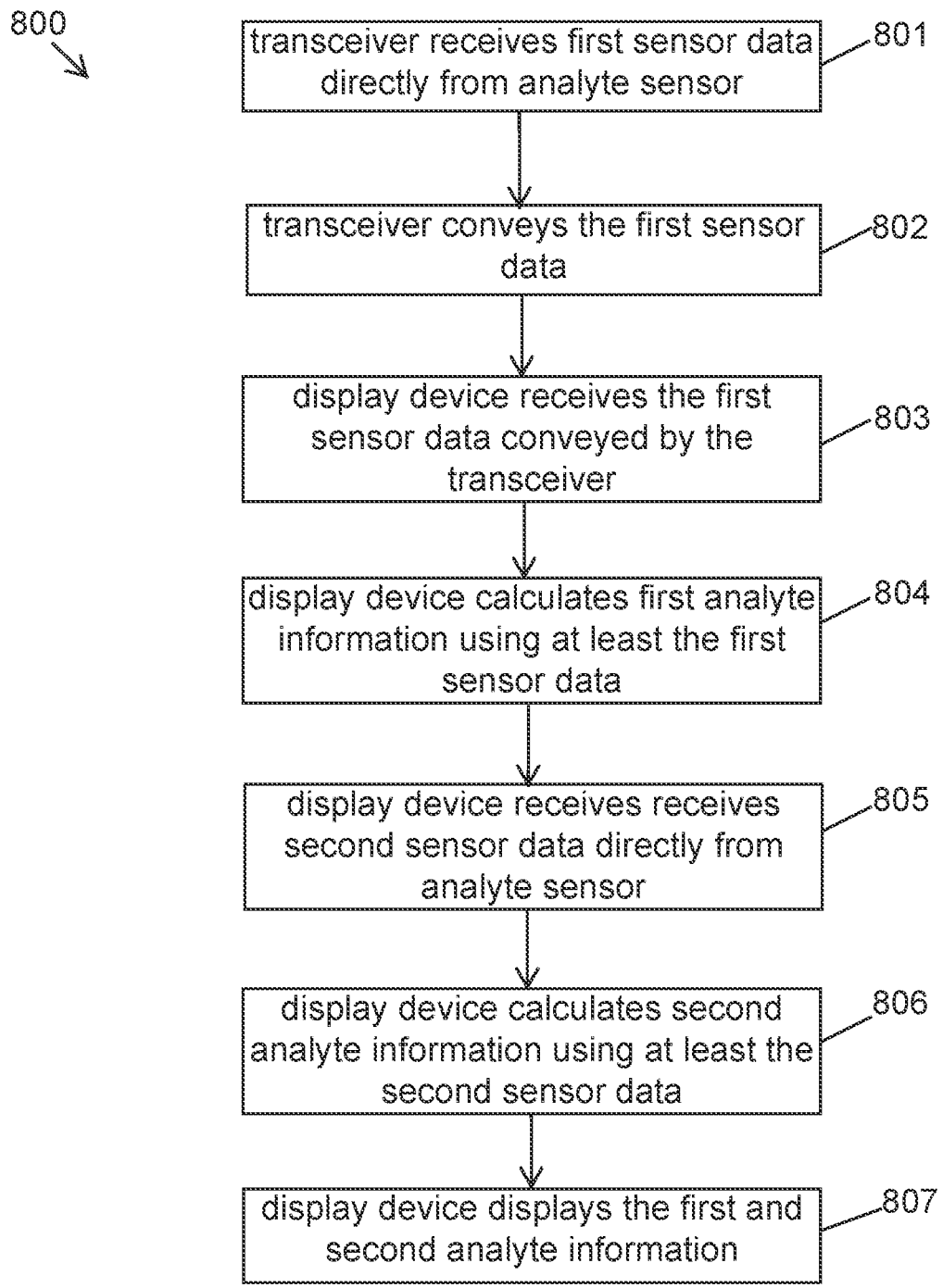
FIG. 10 is a flow chart illustrating a method of using an analyte monitoring system embodying aspects of the present invention.

FIG. 10 is a flow chart illustrating an alternative process 800 embodying aspects of the present invention. The process 800 is similar to the process 700 described above with reference to FIG. 9 except that, while the analyte monitoring system 50 is being used in accordance with the CGM mode, the display device 105 calculates analyte information using sensor data received indirectly from the analyte sensor 100 via the transceiver 101 (instead of receiving from the transceiver 101 analyte information calculated by the transceiver 101 as in step 703 of the process 700). In some embodiments, the process 800 may include one or more steps (e.g., steps 801-803) in which the analyte monitoring system 50 is used according to the CGM mode and one or more steps (e.g., steps 804-805) in which the analyte monitoring system 50 is used according to the FGM mode.

In some embodiments, the process 800 may include a step 801 in which the transceiver 101 receives first sensor data directly from an analyte sensor 100. See description of step 701 above.

In some embodiments, the process 800 may include a step 802 in which the transceiver 101 conveys the first sensor data. In some embodiments, the first sensor data may be conveyed wirelessly. In some embodiments, the transceiver 101 may convey the first sensor data using the wireless communication IC 910. In some embodiments, the transceiver 101 may employ a communication standard (e.g., a Bluetooth™ LE standard) to convey the first sensor data. In some alternative embodiments, the first sensor data may be conveyed using a wired connection (e.g., using a wired connection between the connector 902 of the transceiver 101 and the connector 30 of the display device 105).

In some embodiments, the process 800 may include a step 803 in which the display device 105 receives the first sensor data conveyed by the transceiver 101. In some embodiments, the display device 105 may use the first wireless communication IC 312 to receive the first sensor data conveyed by the transceiver 101.

In some embodiments, the process 800 may include a step 804 in which the display device 105 calculates first analyte information using at least the received first sensor data. In some embodiments, the calculated first analyte information may include one or more of an analyte concentration and an analyte concentration trend. In some embodiments, the step 804 of calculating the first analyte information may include determining if an alert and/or alarm condition exists based on at least the calculated first analyte information (e.g., an analyte concentration and/or analyte concentration trend). In some embodiments, the alert and/or alarm conditions may include one or more of a high analyte alarm level, a low analyte alarm level, a high target analyte level, and a low target analyte level.

In some embodiments, the process 800 may include a step 805 in which the display device 105 to receive second sensor data directly from the analyte sensor 100. See the description of step 705 above.

In some embodiments, the process 800 may include a step 806 in which the display device 105 calculates second analyte information using at least the second sensor data. See description of step 706 above.

In some embodiments, the process 800 may include a step 807 in which the display device 105 displays the first analyte information and the second analyte information. See description of step 707 above.

In some embodiments, the process 800 may include an additional step in which the display device 105 may convey the first analyte information and the second analyte information over a network to a remote device. In some embodiments, the step of conveying the first analyte information and the second analyte information may include the display device 105 using the second wireless communication IC 316 to transmit the first and second sets of analyte information via network, such as for example and without limitation, a wireless local area network (e.g., Wi-Fi), a cellular network, and/or the Internet.

While the process 800 described above is shown in FIG. 10 as a sequence of steps, it should be understood that the sequence of steps may be altered, additional steps may be added, and some steps may be omitted without departing from the scope of the present disclosure. For example, in some alternative embodiments, steps 805 and 806 may be performed before steps 801-804. For another example, in some embodiments, process 800 may include additional steps in which the transceiver 101 receives third sensor data from the analyte sensor 100, the transceiver 101 conveys the third sensor data to the display device 105, the display device 105 calculates third analyte information using at least the third sensor data, and the display device 105 displays the first, second, and third analyte information. For yet another example, the process 800 may include additional steps in which the display device 105, receives fourth sensor data directly from the analyte sensor 100, calculates fourth analyte information, and displays at least the first, second, and fourth analyte information.

Figure 11:
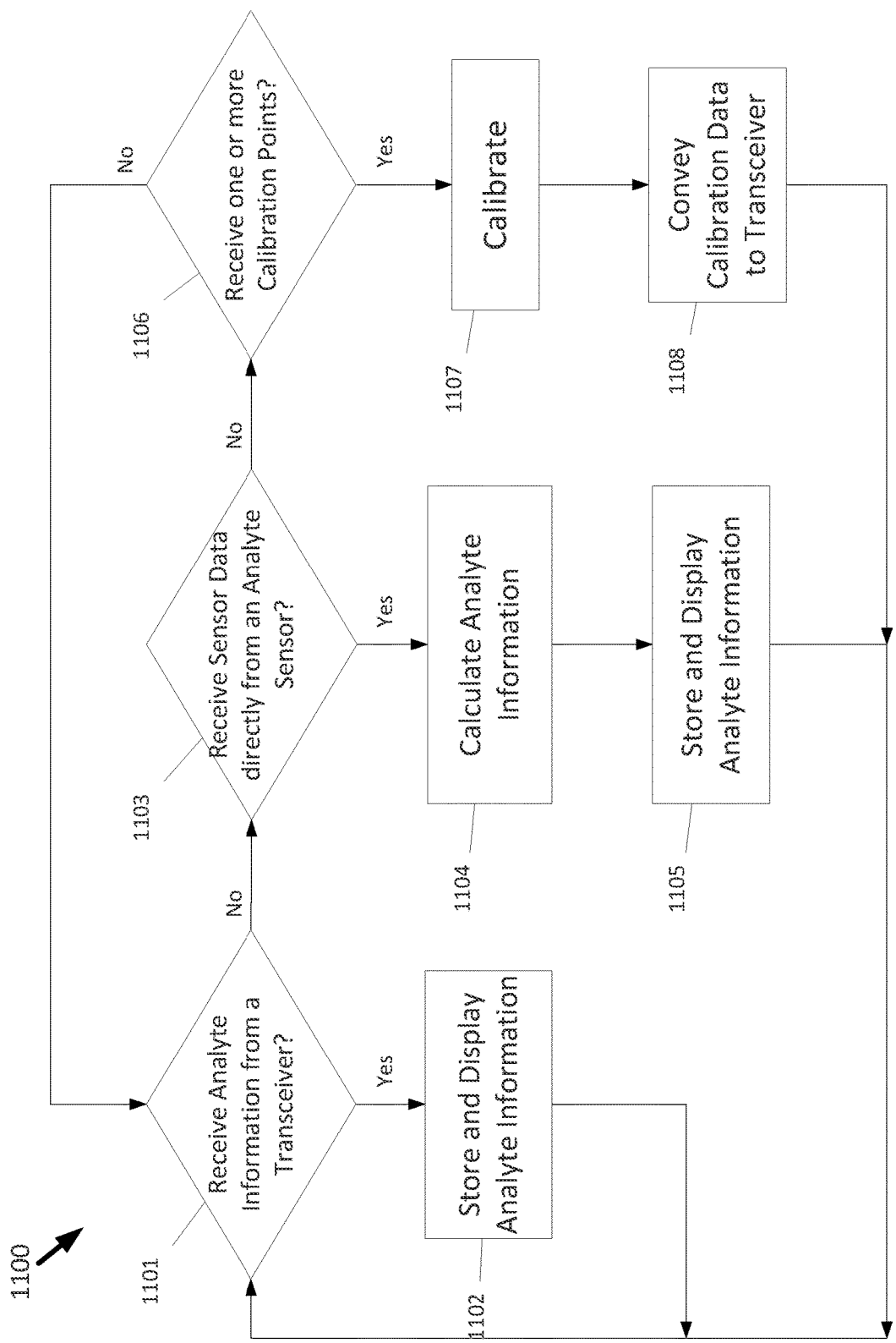
FIG. 11 is a flow chart illustrating a method of using a display device embodying aspects of the present invention

FIG. 11 is a flow chart illustrating a process 1100, which may be executed by a computer 310 in a display device 105, embodying aspects of the present invention. In some embodiments, the process 1100 may include one or more steps (e.g., steps 1101-1102) in which the analyte monitoring system 50 is used according to the CGM mode and one or more steps (e.g., steps 1103-1105) in which the analyte monitoring system 50 is used according to the FGM mode.

In some embodiments, the process 1100 may include a step 1101 in which the display device 105 (e.g., the computer 310 of the display device 105) determines whether the display device 105 has received analyte information conveyed by the transceiver 101. In some embodiments, the analyte information may include one or more of: (i) an analyte concentration, (ii) a time stamp, and (iii) analyte concentration trend information. In some embodiments, the analyte information may additionally or alternatively include one or more of: (i) an alert, (ii) an alarm, and (iii) a notification. In some embodiments, if analyte information has been received from the transceiver 101, the process 1100 may proceed from step 1101 to a step 1102 in which the display device 105 stores the analyte information (e.g., in the memory 314 of the display device 105) and/or displays the analyte information (e.g., using one or more of a display 320, a speaker 324, and a vibration motor 326 of a user interface 340 of the display device 105). In some embodiments, if analyte information from the transceiver 101 has not been received by the display device 105, the process 1100 may proceed from the step 1101 to a step 1103.

In some embodiments, the process 1100 may include a step 1103 in which the display device 105 (e.g., the computer 310 of the display device 105) determines whether the display device 105 has received sensor data directly from the analyte sensor 100. In some embodiments, the sensor data may include one or more of: (i) a measurement of one or more detectable properties of the analyte indicator 106 and (ii) a temperature measurement. In some embodiments, if the display device 105 has received sensor data directly from the analyte sensor 100, the process 1100 may proceed to a step 1104 in which the display device 105 (e.g., the computer 310 of the display device 105) calculates analyte information using at least the sensor data received directly from the analyte sensor 100 (see description of step 705 of FIG. 7 above) and then to a step 1105 in which the display device 105 stores the analyte information (e.g., in a memory 314 of the display device 105) and/or displays the analyte information (e.g., using one or more of a display 320, a speaker 324, and a vibration motor 326 of a user interface 340 of the display device 105). In some embodiments, as illustrated in FIG. 11, the process 1100 may proceed from step 1105 back to step 1101. However, this is not required, and, in some alternative embodiments, the process 1100 may proceed from step 1105 to a step 1106. In some embodiments, if the display device 105 has not received sensor data directly from an analyte sensor 100, the process 1100 may proceed from the step 1103 to a step 1106.

In some embodiments, the step 1104 of calculating analyte information may include calculating an analyte concentration and/or an analyte concentration trend using at least the received sensor data. In some embodiments, the step 1104 of calculating the analyte information includes determining if an alert and/or alarm condition exists based on the calculated analyte concentration and/or analyte concentration trend. In some embodiments, the alert and/or alarm conditions include one or more of a high analyte alarm level, a low analyte alarm level, a high target analyte level, and a low target analyte level.

In some embodiments, the process 1100 may include a step 1106 in which the display device 105 (e.g., the computer 310 of the display device 105) determines whether one or more calibration points have been received by the user interface 340 of the display device 105 (e.g., by the user input 322 of the user interface 340). In some embodiments, the one or more calibration points may include one or more reference measurements (e.g., one or more self-monitoring blood glucose (SMBG) measurements). In some embodiments, if one or more calibration points have been received by the user interface 340 of the display device 105, the process 1100 may proceed from the step 1106 to a step 1107 in which the display device 105 performs a calibration of conversion of sensor data to analyte information using at least the one or more calibration points and a step 1108 in which the display device 105 conveys the one or more calibration points to the transceiver 101. In some embodiments, if one or more calibration points have not been received by the display device 105, the process 1100 may from the step 1106 back to step 1101.

Figure 12:
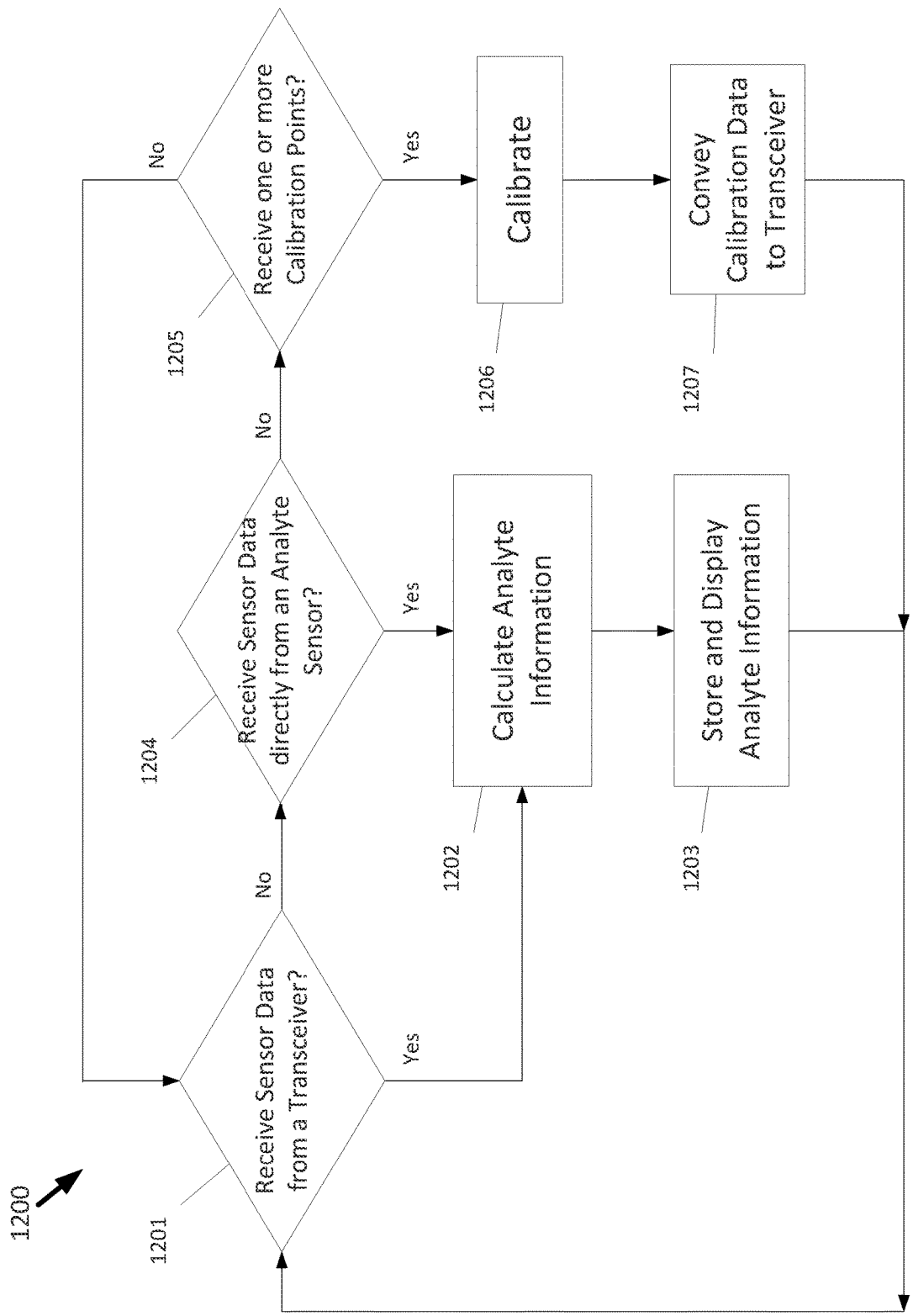
FIG. 12 is a flow chart illustrating a method of using a display device embodying aspects of the present invention.

FIG. 12 is a flow chart illustrating a process 1200, which may be executed by a computer 310 in a display device 105, embodying aspects of the present invention. The process 1200 is similar to the process 1100 described above with reference to FIG. 11 except that, while the analyte monitoring system 50 is being used in accordance with the CGM mode, the display device 105 calculates analyte information using sensor data received indirectly from the analyte sensor 100 via the transceiver 101 (instead of receiving from the transceiver 101 analyte information calculated by the transceiver 101 as in step 1101 of process 1100). In some embodiments, the process 1200 may include one or more steps (e.g., step 1201) in which the analyte monitoring system 50 is used according to the CGM mode and one or more steps (e.g., step 1104) in which the analyte monitoring system 50 is used according to the FGM mode.

In some embodiments, the process 1200 may include a step 1201 in which the display device 105 (e.g., the computer 310 of the display device 105) determines whether the display device 105 has received sensor data conveyed by the transceiver 101. In some embodiments, if the display device 105 has received sensor data from the transceiver 101, the process 1200 may proceed to a step 1202 of calculating analyte information and a step 1203 of storing and/or displaying the analyte information. In some embodiments, if the display device 105 has not received sensor data from the transceiver 101, the process 1200 may proceed from the step 1201 to a step 1204.

In some embodiments, the process 1200 may include a step 1204 of determining whether the display device 105 has received sensor data directly from the analyte sensor 100. In some embodiments, if the display device 105 has received sensor data directly from the analyte sensor 100, the process 1200 may proceed from the step 1204 to the step 1202 of calculating analyte information and the step 1203 of storing and/or displaying the analyte information. In some embodiments, if the display device 105 has not received sensor data directly from the analyte sensor 100, the process 1200 may proceed from the step 1204 to a step 1205.

In some embodiments, the process 1200 may include a step 1202 in which the display device 105 (e.g., the computer 310 of the display device 105) calculates analyte information using at least the sensor data received (a) indirectly from the analyte sensor 100 via the transceiver 101 in the step 1201 or (b) directly from the analyte sensor 100 in step 1204. In some embodiments, calculating the analyte information in step 1202 may include calculating an analyte concentration and/or an analyte concentration trend using at least the received sensor data. In some embodiments, the step 1202 of calculating the analyte information may include determining if an alert and/or alarm condition exists based on the calculated analyte concentration and/or the analyte concentration trend. In some embodiments, the alert and/or alarm conditions include one or more of a high analyte alarm level, a low analyte alarm level, a high target analyte level, and a low target analyte level. In some embodiments, the process 1200 may proceed from the step 1202 to a step 1203.

In some embodiments, the process 1200 may include a step 1203 in which the display device 105 stores the analyte information (e.g., in a memory 314 of the display device 105) and/or displaying the analyte information (e.g., using one or more of a display 320, a speaker 324, and a vibration motor 326 of a user interface 340 of the display device 105). In some embodiments, as shown in FIG. 12, the process 1200 may proceed from step 1203 back to the step 1201. However, this is not required, and, in some alternative embodiments, the process 1200 may proceed from step 1203 to the step 1205.

In some embodiments, the process 1200 may include a step 1205 in which the display device 105 (e.g., the computer 310 of the display device 105) determines whether one or more calibration points have been received by the user interface 340 of the display device 105 (e.g., by the user input 322 of the user interface 340). In some embodiments, the one or more calibration points include one or more reference measurements (e.g., one or more self-monitoring blood glucose (SMBG) measurements). In some embodiments, if the display device 105 has received one or more calibration points, the process 1200 may proceed from the step 1205 to a step 1206 in which the display device 105 performs a calibration of the conversion of sensor data to analyte information using at least the one or more calibration points and a step 1207 in which the display device 105 conveys the one or more calibration points to the transceiver 101. However, in some alternative embodiments, the process 1200 may not include the step 1207, and the process 1200 may proceed from step 1206 back to step 1201. In some of these alternative embodiments, the transceiver 101 may not calculate analyte information and, therefore, would not require the one or more calibration points. In some embodiments, if one or more calibration points have not been received by the display device 105, the process 1200 may proceed from step 1205 back to step 1201.

While the processes 1100 and 1200 are illustrated in FIGS. 11 and 12, respectively, as sequences of steps, it should be understood that the sequence of steps may be altered, additional steps may be added, and some steps may be omitted without departing from the scope of the present disclosure. For example, the steps of processes 1100 and 1200 may be performed in a different order.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. An analyte monitoring system comprising:
   an analyte sensor including an analyte indicator that exhibits one or more detectable properties based on an amount or concentration of an analyte in proximity to the analyte indicator;
   a transceiver configured to:
      receive first sensor data directly from the analyte sensor,
      generate first analyte information using at least the received first sensor data, wherein generating the first analyte information comprises calculating a first analyte concentration using at least the received first sensor data, and
      convey the first analyte information; and
   a display device configured to:
      receive second sensor data directly from the analyte sensor,
      generate second analyte information using at least the received second sensor data, wherein generating the second analyte information comprises calculating a second analyte concentration using at least the received second sensor data,
      receive the first analyte information conveyed by the transceiver, and
      display the first and second analyte concentrations.

2. The analyte monitoring system of claim 1, wherein the display device comprises a first wireless communication integrated-circuit (IC) and a second wireless communication IC, the first communication IC is configured to employ a first standard to communicate wirelessly, the second communication IC is configured to employ a second standard to communicate wirelessly, and the second standard is different than the first standard.

3. The analyte monitoring system of claim 2, wherein the first standard is a Bluetooth standard, and the second standard is a near field communication (NFC) standard.

4. The analyte monitoring system of claim 2, wherein the display device is configured to use the first wireless communication IC to receive the first analyte information conveyed by the transceiver and to use the second wireless communication IC to receive the second sensor data directly from the analyte sensor.

5. The analyte monitoring system of claim 2, wherein the display device comprises a third wireless communication IC, and the display device is configured to use the third wireless communication IC to convey the first and second analyte information over a network to a remote device.

6. The analyte monitoring system of claim 1, wherein the transceiver is configured to be worn by a host using the analyte sensor while the transceiver receives the first sensor data directly from the analyte sensor.

7. The analyte monitoring system of claim 1, wherein one or more of the first and second analyte information comprises one or more of: (i) a time stamp and (ii) analyte concentration trend information.

8. The analyte monitoring system of claim 1, wherein one or more of the first and second analyte information comprises one or more of: (i) an alert, (ii) an alarm, and (iii) a notification.

9. The analyte monitoring system of claim 1, wherein the first sensor data comprises one or more of: (i) a measurement of the one or more detectable properties and (ii) a temperature measurement.

10. The analyte monitoring system of claim 1, wherein the display device comprises a graphical user interface and is configured to generate an alert or alarm on the graphical user interface of the display device.

11. The analyte monitoring system of claim 1, wherein the transceiver comprises a graphical user interface and is configured to generate an alert or alarm on the graphical user interface of the transceiver.

12. The analyte monitoring system of claim 1, wherein the display device is configured to convey the second analyte information to the transceiver, and the transceiver is configured to receive the second analyte information.

13. The analyte monitoring system of claim 1, wherein the display device is configured to receive one or more calibration points.

14. The analyte monitoring system of claim 13, wherein the display device is configured to perform an analyte information calibration using at least the one or more calibration points.

15. The analyte monitoring system of claim 13, wherein the display device is configured convey the one or more calibration points, and the transceiver is configured to receive the one or more calibration points and perform an analyte information calibration using at least the one or more calibration points.

16. A method comprising:
(a) using a transceiver of an analyte monitoring system to receive first sensor data directly from an analyte sensor of the analyte monitoring system;
(b) using the transceiver to generate first analyte information using at least the first sensor data, wherein generating the first analyte information comprises calculating a first analyte concentration using at least the received first sensor data;
(c) using the transceiver to convey the first analyte information;
(d) using a display device of the analyte monitoring system to receive the first analyte information conveyed by the transceiver;
(e) using the display device to receive second sensor data directly from the analyte sensor;
(f) using the display device to generate second analyte information using at least the received second sensor data, wherein generating the second analyte information comprises calculating a second analyte concentration using at least the received second sensor data; and
(g) using the display device to display the first analyte information and the second analyte concentrations.

17. The method of claim 16, wherein the step (a) comprises positioning the transceiver such that the transceiver is operatively linked to the analyte sensor.

18. The method of claim 17, wherein positioning the transceiver includes wearing, by a host using the analyte sensor, the transceiver externally on an armband, a wrist band, a waist band, or an adhesive patch.

19. The method of claim 16, wherein the step (e) comprises positioning the display device such that the display device is operatively linked to analyte sensor.

20. The method of claim 16, wherein the display device comprises a first wireless communication IC and a second wireless communication IC, the first communication IC is configured to employ a first standard to communicate wirelessly, the second communication IC is configured to employ a second standard to communicate wirelessly, and the second standard is different than the first standard.

21. The method of claim 20, wherein the first standard is a Bluetooth standard, and the second standard is a near field communication (NFC) standard.

22. The method of claim 20, wherein the step (c) comprises using the first communication IC of the display device to receive the first analyte information conveyed by the transceiver.

23. The method of claim 20, wherein the step (e) comprises using the second communication IC of the display device to receive the second sensor data directly from the analyte sensor.

24. The method of claim 20, wherein the display device comprises a third wireless communication IC, and the method further comprises:
(h) using the third wireless communication of the display device to convey the first analyte information and the second analyte information over a network to a remote device.

25. The method of claim 16, wherein the step (e) comprises removing the transceiver away from the analyte sensor such that the transceiver is not operatively linked to the analyte sensor.

26. The method of claim 16, wherein one or more of the first and second analyte information comprises one or more of: (i) a time stamp and (ii) analyte concentration trend information.

27. The method of claim 16, wherein one or more of the first and second analyte information comprises one or more of: (i) an alert, (ii) an alarm, and (iii) a notification.

28. The method of claim 16, wherein the first sensor data comprises one or more of: (i) a measurement of one or more detectable properties exhibited by an analyte indicator of the analyte sensor based on an amount or concentration of an analyte in proximity to the analyte indicator and (ii) a temperature measurement.

29. The method of claim 16, wherein the display device comprises a graphical user interface and is configured to generate an alert or alarm on the graphical user interface of the display device.

30. The method of claim 16, wherein the transceiver comprises a graphical user interface and is configured to generate an alert or alarm on the graphical user interface of the transceiver.

31. The method of claim 16, further comprising:
using the display device to convey the second analyte information; and
using the transceiver to receive the second analyte information conveyed by the display device.

32. The method of claim 16 further comprising using the display device to receive one or more calibration points.

33. The method of claim 32, further comprising using the display device to perform an analyte information calibration using at least the one or more calibration points.

34. The method of claim 32 further comprising:
using the display device to convey the one or more calibration points; and
using the transceiver to receive the one or more calibration points conveyed by the display device and perform an analyte information calibration using at least the one or more calibration points.

* * * * *